US012765852B2

(12) United States Patent
Kotecha et al.

(10) Patent No.: US 12,765,852 B2
(45) Date of Patent: Oct. 20, 2026

(54) ANIMAL TEMPERATURE CONTROL APPARATUS, SYSTEM, AND METHODS THEREOF

(71) Applicant: O2M Technologies, LLC, Chicago, IL (US)

(72) Inventors: Mrignayani Kotecha, Chicago, IL (US); Boris Meerovich Epel, Chicago, IL (US); Marcelo Gutierrez-Miranda, Chicago, IL (US)

(73) Assignee: O2M Technologies, LLC, Chicago, IL (US)

( * ) Notice: Subject to any disclaimer, the term of this patent is extended or adjusted under 35 U.S.C. 154(b) by 307 days.

(21) Appl. No.: 18/706,804

(22) PCT Filed: Nov. 8, 2022

(86) PCT No.: PCT/US2022/079482

§ 371 (c)(1),
(2) Date: May 2, 2024

(87) PCT Pub. No.: WO2023/086791

PCT Pub. Date: May 19, 2023

(65) Prior Publication Data

US 2025/0288270 A1 Sep. 18, 2025

Related U.S. Application Data

(60) Provisional application No. 63/277,344, filed on Nov. 9, 2021.

(51) Int. Cl.

*A61B 6/50* (2024.01)
*A01K 1/00* (2006.01)
*A61B 6/04* (2006.01)

(52) U.S. Cl.

CPC ............ *A61B 6/508* (2013.01); *A01K 1/0076* (2013.01); *A61B 6/045* (2013.01); *A61B 2503/40* (2013.01)

(58) Field of Classification Search

CPC ..... A61B 6/508; A61B 6/045; A61B 2503/40; A61B 2503/42; A01K 1/0076; A01K 1/0047; A01K 1/0313

(Continued)

(56) References Cited

U.S. PATENT DOCUMENTS 10,646,320 B1 5/2020 Leevy et al.
2010/0269260 A1* 10/2010 Lanz ........................ A61D 3/00 600/407

FOREIGN PATENT DOCUMENTS

CN 205181525 U 4/2016
CN 113598709 A 11/2021

(Continued)

OTHER PUBLICATIONS

"International Application Serial No. PCT/US2022/079482, International Search Report mailed Mar. 29, 2023", 4 pgs.

(Continued)

*Primary Examiner* — Beverly M Flanagan
(74) *Attorney, Agent, or Firm* — Charles A. Lemaire; Lemaire Patent Law Firm, P.L.L.C.

(57) ABSTRACT

Provided herein are apparatuses, systems, and methods of controlling the temperature of an animal being imaged under anesthesia. For example, the animal is placed under anesthesia on an animal bed apparatus within an imaging system, the temperature of a conditioned air flow from the air injector via a temperature control apparatus is measured using an air temperature sensor, the temperature of the animal's body is measured using an animal temperature sensor, the temperature of the conditioned air flow to the (Continued)

animal and the temperature of the animal's body is monitored using a controller in communication with a temperature control apparatus, air temperature sensor, and animal temperature sensor, and the temperature of the conditioned air directed over the animal is automatically adjusted using the temperature control apparatus.

37 Claims, 24 Drawing Sheets

(58) Field of Classification Search
USPC .............................................................. 607/96
See application file for complete search history.

(56) References Cited

FOREIGN PATENT DOCUMENTS

| | | | | | |
|---|---|---|---|---|---|
| DE | 102014003115 | A1 | | 10/2015 | |
| WO | WO-2007135248 | A1 | * | 11/2007 | ............. A61B 5/704 |
| WO | WO-2008142593 | A2 | * | 11/2008 | ............... A61D 7/04 |
| WO | WO-2023086791 | A1 | | 5/2023 | |

OTHER PUBLICATIONS

"International Application Serial No. PCT/US2022/079482, Invitation to Pay Additional Fees mailed Jan. 10, 2023", 2 pgs.
"International Application Serial No. PCT/US2022/079482, Written Opinion mailed Mar. 29, 2023", 7 pgs.

* cited by examiner

ANIMAL TEMPERATURE CONTROL APPARATUS, SYSTEM, AND METHODS THEREOF

CROSS-REFERENCE TO RELATED APPLICATIONS

This application is a U.S. National Stage Filing under 35 U.S.C. § 371 from International Application No. PCT/US2022/079482, filed on Nov. 8, 2022, and published as WO2023/086791 on May 19, 2023, which claims priority to U.S. Provisional Application No. 63/277,344, filed Nov. 9, 2021; the benefit of priority of each of which is hereby claimed herein, and which applications and publication are hereby incorporated herein by reference in their entireties.

FIELD

The present disclosure relates generally to an animal temperature control apparatus, an animal bed, and systems and methods thereof. In at least one example, the present disclosure relates to a system with an animal bed and temperature control apparatus and methods to adjust the temperature of the animal being imaged under anesthesia.

BACKGROUND

Small animal imaging experiments are necessary in developing and validating new science. The imaging is also an important step in translating important findings from lab to clinical applications. During preparation and imaging sessions, animals are often anesthetized for immobilization. Hypothermia and/or mortality of small animals due to anesthesia during imaging is a known problem. Under anesthesia, animals reduce the ability for the thermal regulation and need active heating to maintain their temperature. Pulse electron paramagnetic resonance oxygen imaging (EPROI) is an emerging imaging modality that provides three-dimensional partial oxygen pressure ($pO_2$) maps in live tissues. Oxygen imaging using EPROI requires anesthetizing animals during the measurement. For operation inside an oxygen imager, a non-magnetic temperature control system is required which necessitates location of heating elements outside of the imager. This increases thermal inertia of the system and reduces its ability to quickly react on the temperature changes. During oxygen imaging, radiofrequency pulses deposit heat in the animals. Anesthesia also affects the animal oxygenation, therefore, animal's respiration must be monitored during the imaging session. Therefore, a complex agile animal temperature control and respiratory monitoring system that may react fast and precisely is needed for oxygen imaging experiments.

As presented herein, a system has been developed to help maintain the animal's temperature while being imaged under anesthesia.

BRIEF SUMMARY

Provided herein is a temperature control apparatus for heating or cooling an animal under anesthesia for imaging. The apparatus includes: a cooling fan operatively connected to a cooling air line; a heating fan operatively connected to a heating air line; a heating block operatively connected to the heating fan and the heating air line to heat the air within the heating air line; and a housing, wherein the cooling fan, heating fan, and heating block are located within the housing.

Further provided herein is a system for heating or cooling an animal under anesthesia for imaging. The system includes: a temperature control apparatus having: a cooling fan operatively connected to a cooling air line; a heating fan operatively connected to a heating air line; a heating block operatively connected to the heating fan and the heating air line to heat the air within the heating air line; and a housing, wherein the cooling fan, the heating fan, and the heating block are located within the housing; an air temperature sensor operable to measure the temperature of a conditioned air flow from the cooling air line and the heating air line; an animal temperature sensor operable to measure the temperature of the animal's body; and a controller in communication with the temperature control apparatus, the air temperature sensor, and the animal temperature sensor, and operable to monitor the temperature of the conditioned air flow to the animal and the temperature of the animal's body.

Also provided herein is an animal bed apparatus for imaging. The animal bed apparatus may include: an animal bed comprising: a support surface having a first longitudinal side and a second longitudinal side, wherein the support surface is operable to hold an animal; and a pair of rails along at least a portion of the first longitudinal side and the second longitudinal side; a mask connected to the animal bed and operable to hold anesthesia over the animal; an anesthesia inlet operably connected to the mask and operable to be connected to an anesthesia source via an anesthesia line; a base comprising rail slots along a first longitudinal edge and a second longitudinal edge, wherein the rail on the portion of the first longitudinal side of the animal bed surface is operable to slide within the rail slot along the first longitudinal edge of the base and the rail on the portion of the second longitudinal side of the animal bed surface is operable to slide within the rail slot along the second longitudinal edge of the base; and an air injector connected to the base and operable to blow conditioned air over the animal on the animal bed.

Additionally provided herein is an animal bed system for maintaining an animal's temperature while being imaged under anesthesia. The system may include: a temperature control apparatus comprising: a cooling fan operatively connected to a cooling air line; a heating fan operatively connected to a heating air line; and a heating block operatively connected to the heating fan and the heating air line to heat the air within the heating air line; an animal bed apparatus operable to hold an animal, the animal bed apparatus having a base comprising: a cooling air line inlet, a heating air line inlet, an injection zone operable to combine air from the cooling air line and the heating air line, creating conditioned air, and an air injector operable to direct the conditioned air over the animal, wherein the cooling air line is connected to the cooling air line inlet and the heating air line is connected to the heating air line inlet; an air temperature sensor operable to measure the temperature of the conditioned air from the air injector; an animal temperature sensor operable to measure the temperature of the animal's body; and a controller in communication with the temperature control apparatus, the air temperature sensor, and the animal temperature sensor, and operable to monitor the temperature of the conditioned air to the animal and the temperature of the animal's body.

Further provided herein is a method for maintaining an animal's temperature while being imaged under anesthesia. The method may include: placing the animal on an animal bed apparatus, the animal bed apparatus having a base comprising: a cooling air line inlet, a heating air line inlet, an injection zone operable to combine air from the cooling air line and the heating air line, creating conditioned air, and an air injector operable to direct the conditioned air over the animal; measuring a temperature of the conditioned air from the air injector using an air temperature sensor; measuring a temperature of the animal's body using an animal temperature sensor; monitoring the temperature of the conditioned air to the animal and the temperature of the animal's body using a controller in communication with an temperature control apparatus, the air temperature sensor, and the animal temperature sensor; and adjusting the temperature of the conditioned air directed over the animal using the temperature control apparatus, the temperature control apparatus comprising: a cooling fan operatively connected to a cooling air line; a heating fan operatively connected to a heating air line; and a heating block operatively connected to the heating fan and the heating air line to heat the air within the heating air line, wherein the cooling air line is connected to the cooling air line inlet and the heating air line is connected to the heating air line inlet.

Yet further provided herein is a method of imaging an animal under anesthesia in a controlled temperature environment. The method may include: placing the animal under anesthesia on an animal bed apparatus; placing the animal bed apparatus with the animal within an imaging system; measuring the temperature of conditioned air from an air injector on the animal bed apparatus using an air temperature sensor; measuring the temperature of the animal's body using an animal temperature sensor; monitoring the temperature of the conditioned air to the animal and the temperature of the animal's body using a controller in communication with a temperature control apparatus, the air temperature sensor, and the animal temperature sensor; and adjusting the temperature of the conditioned air directed over the animal using the temperature control apparatus.

Other aspects and iterations of the invention are described more thoroughly below.

BRIEF DESCRIPTION OF THE DRAWINGS

Implementations of the present technology will now be described, by way of example only, with reference to the attached figures, wherein.

DETAILED DESCRIPTION

Figure 1:
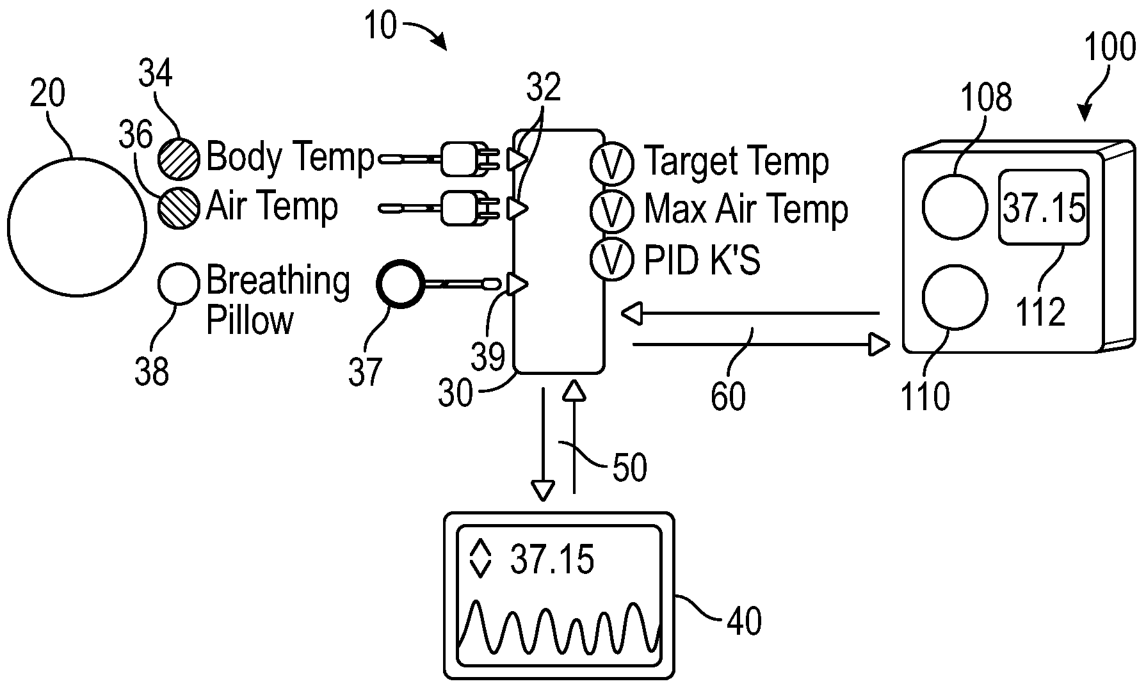
FIG. 1 is an overview of a temperature control system in one example.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented. The terms "connected" or "coupled" is defined as connected, whether directly or indirectly through intervening components, and is not necessarily limited to physical connections. The connection may be such that the objects are permanently connected, releasably connected, or wirelessly connected.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Thus, references to one or an embodiment in the present disclosure may be references to the same embodiment or any embodiment; and such references mean at least one of the embodiments.

The terms "comprising," "including" and "having" are used interchangeably in this disclosure. The terms "comprising," "including" and "having" mean to include, but not necessarily be limited to the things so described.

As used herein, "about" refers to numeric values, including whole numbers, fractions, percentages, etc., whether or not explicitly indicated. The term "about" generally refers to a range of numerical values, for instance, ±0.5-1%, ±1-5% or ±5-10% of the recited value, that one would consider equivalent to the recited value, for example, having the same function or result.

As used herein, "imaging system" and "resonator" may be used interchangeably. In an aspect, the imaging system may be an oxygen imaging system that comprises a resonator such as magnetic resonance imaging (MRI), positron emission tomography (PET), computed tomography (CT), or pulse electron paramagnetic resonance oxygen imaging (EPROI) imaging systems. For example, the imaging system may be configured for EPROI.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term.

Small animal (e.g. rodent) imaging experiments are necessary step in developing and validating new science and an important step in translating important findings to clinical applications. Commonly used imaging methodologies are magnetic resonance imaging (MRI), positron emission tomography (PET), computed tomography (CT), and pulse electron paramagnetic resonance oxygen imaging (EPROI).

Oxygen is a key physiological parameter. It has been known that hypoxia or low oxygen is a key biomarker of most cancers and cancer response to the therapy is dependent on oxygenation status. It is also known that hypoxia is the major limiting factor in the success of cell therapies and artificial tissue grafts. Small animal (e.g. mice and rat) EPROI experiments are crucial for understanding biology, designing new therapies, defining new strategies in cancer and regenerative medicine.

EPROI is an emerging preclinical imaging modality that provides partial oxygen pressure (pO2) maps with high temporal, spatial, and pO2 resolution. The pO2 maps obtained using EPROI are used for important insights into oxygen dynamics with applications in cancer, type I diabetes, tissue engineering and regenerative medicine. In recent studies, pO2 maps were used for assistance in oxygen guided radiation therapy (OGRT), assessment of islet encapsulation devices, assessment of anti-cancer drug, detection of mitochondrial dysfunction, and assessment of musculoskeletal tissue grafts. EPROI in combination with the temperature control system described herein below may be used to image a non-human animal. The whole body or any tissue besides brain tissue may be imaged.

During imaging, such as with EPROI, animals are anesthetized to reduce their mobility during imaging. Anesthesia affects animals' thermal regulation and thus necessitates external control of their temperature. Therefore, it is important to supply heat during the time when animal is under anesthesia. EPROI, like MRI, is a magnetic resonance technique. A set of precise magnetic field are applied to the imaging object. The presence of magnetic items or coils with the flowing currents can affect the spatial fidelity of the images and should be avoided. Therefore, nonmagnetic heat delivery systems based on air or water flow are mandated. Current MR compatible temperature control systems for small animals perform a long-term stabilization, but they exhibit a common problem of slow response time due to remote location of the heating element. This is not suitable for oxygen imaging because of two reasons. Solubility of oxygen in tissues is temperature dependent, thus precise body temperature should be maintained for reproducible results. The second problem is related to the heat deposition primarily due to dissipation of the radio frequency magnetic field during imaging sequence in tissues. This is especially important for full body mouse imaging since there is no natural sink for the energy available. Therefore, temperature control systems must adapt to the rapid heat deposition changes between imaging and not imaging states. In addition, oxygenation in animal is dependent on anesthesia and therefore, animals need to be maintained under lighter anesthesia necessitating the closer monitoring of respiratory system. All these problems require a smart agile animal life support system that can react fast and precisely to support animal well-being during the oxygen imaging experiments.

Temperature Control Apparatus

Figure 2:
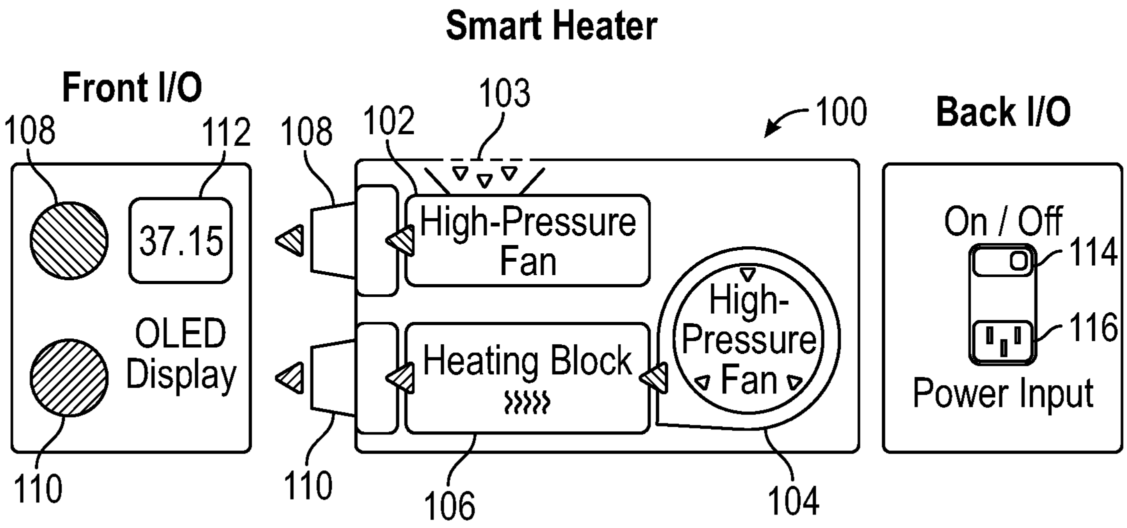
FIG. 2 is a temperature control apparatus in one example.
Figure 3A:
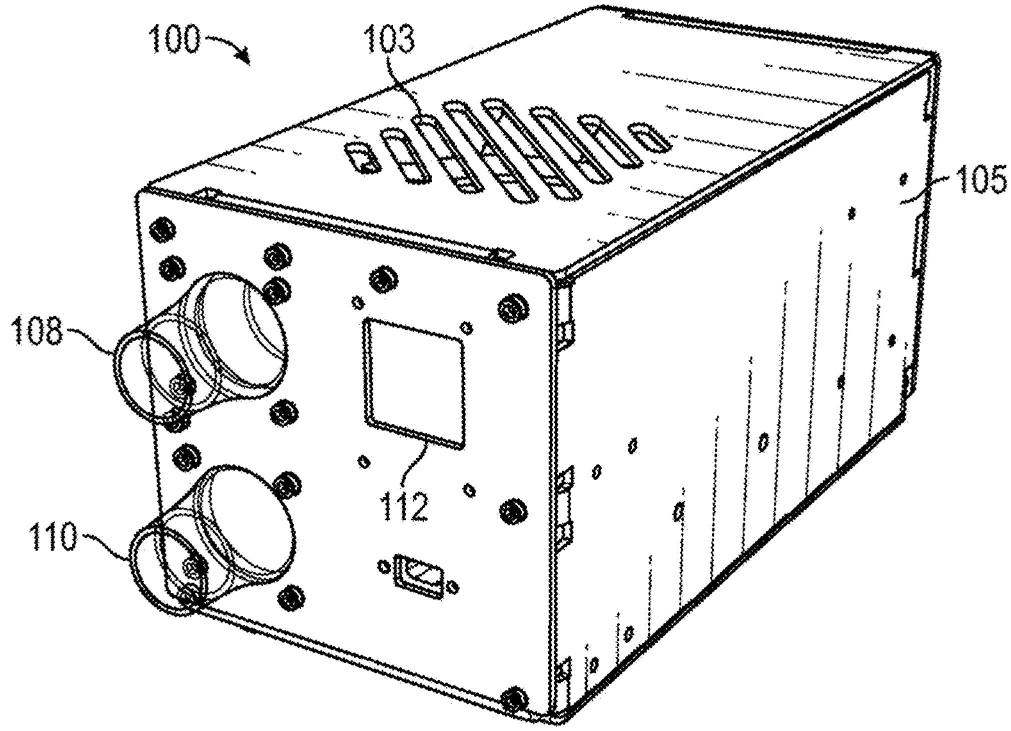
FIG. 3A is an isometric view of a temperature control apparatus in one example.
Figure 3B:
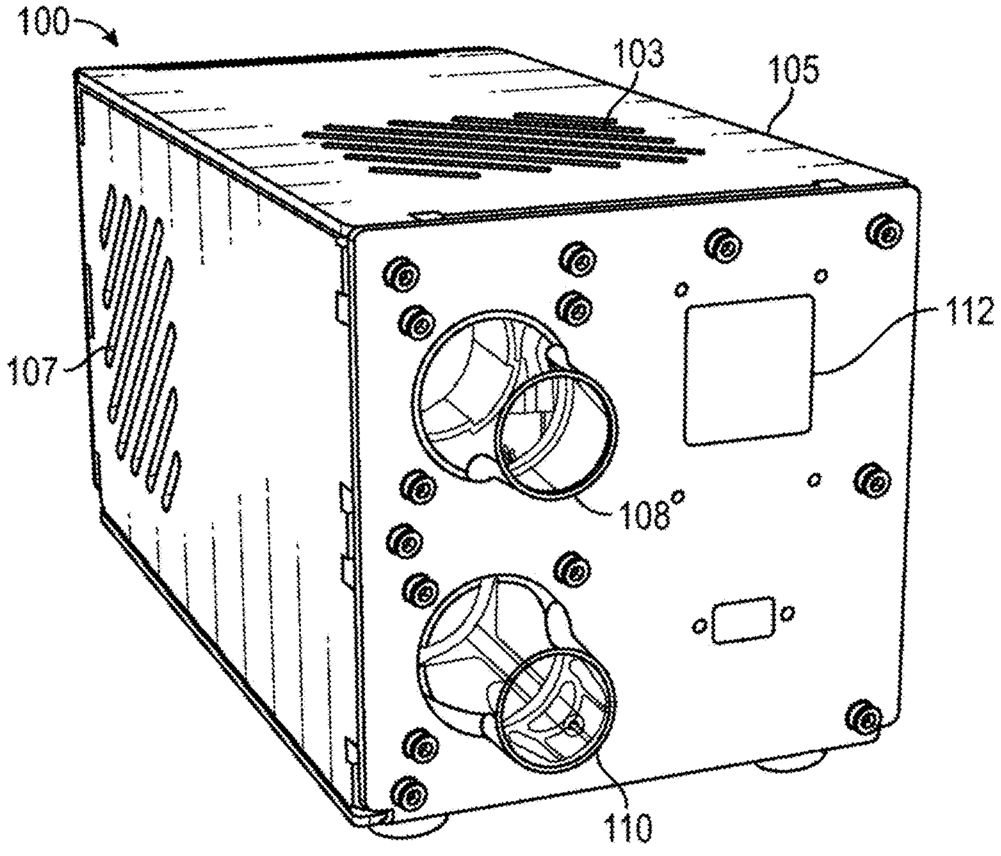
FIG. 3B is an isometric view of a temperature control apparatus in one example.
Figure 4A:
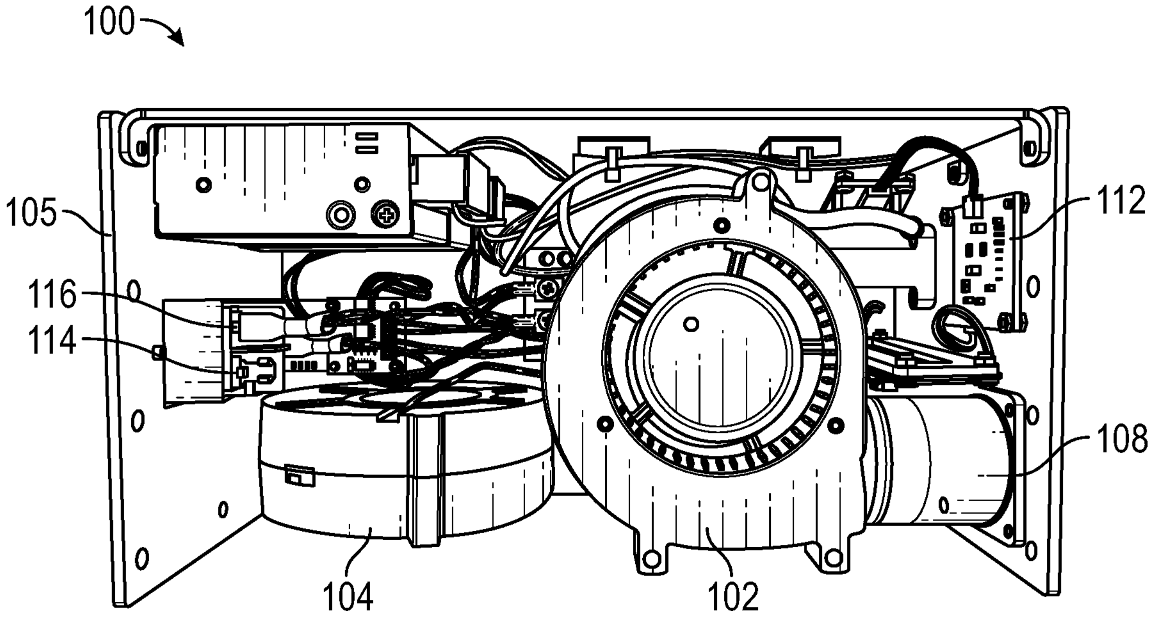
FIG. 4A is a top view of a temperature control apparatus with the top and side of the housing removed in one example.
Figure 4B:
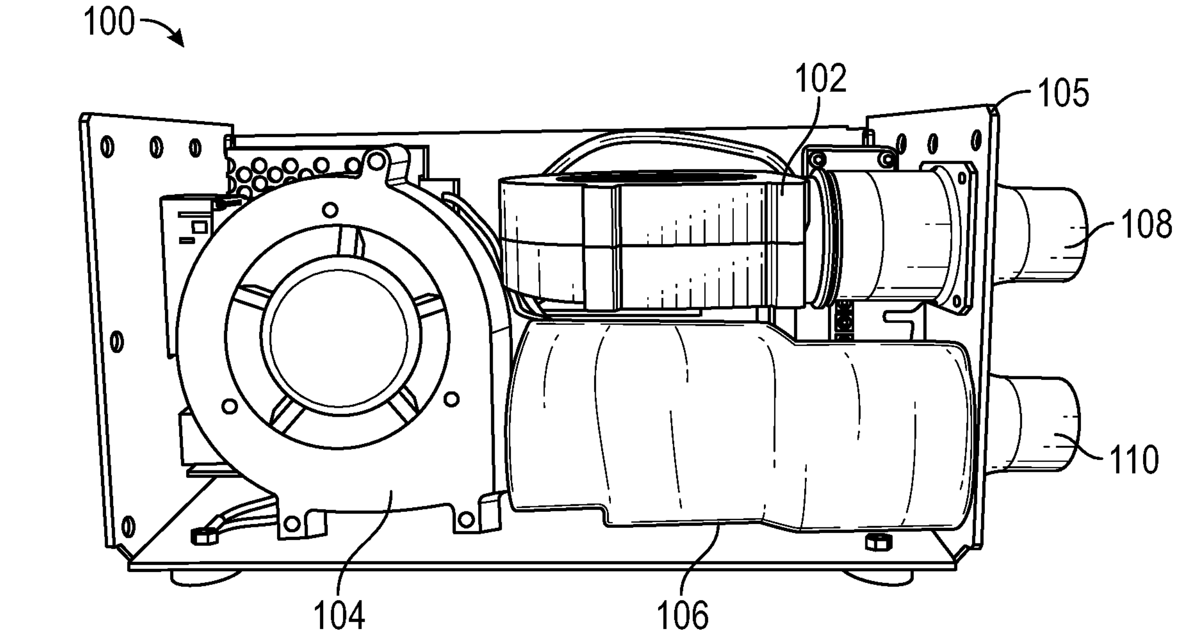
FIG. 4B is a side view of a temperature control apparatus with the top and side of the housing removed in one example.
Figure 4C:
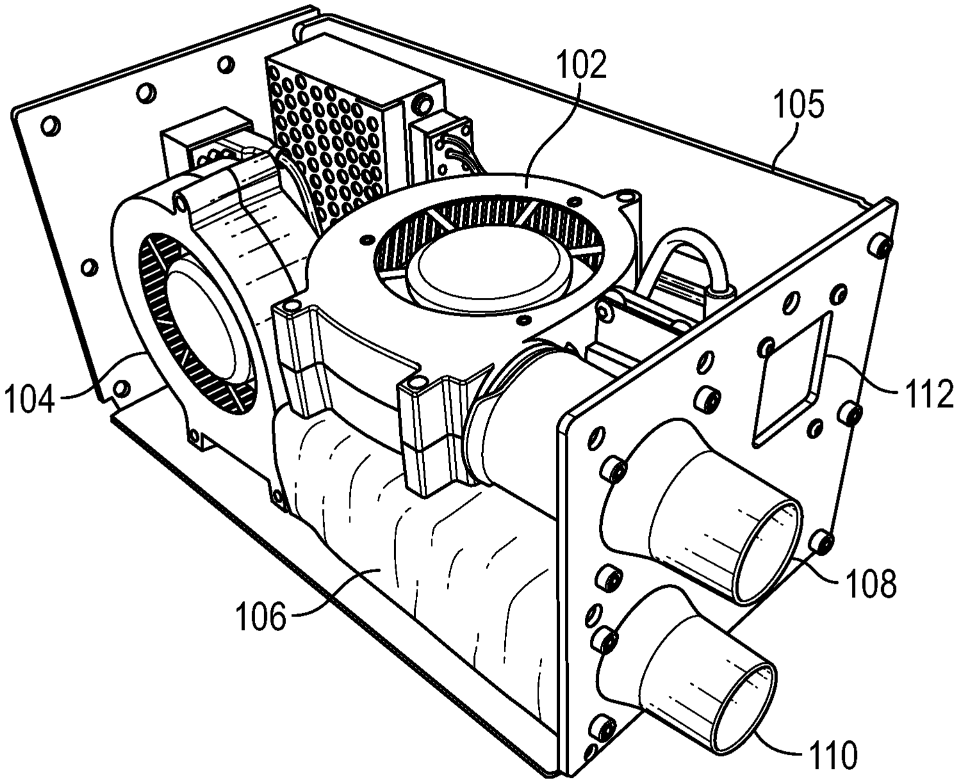
FIG. 4C is an isometric view of a temperature control apparatus with the top and side of the housing removed in one example.

Provided herein is a temperature control apparatus 100 for heating or cooling an animal under anesthesia for imaging. The imaging may include, MRI, PET, CT, EPROI or other imaging methods known in the art. FIG. 2 shows a schematic drawing of the temperature control apparatus 100 and FIG. 1 shows a temperature control system 10 with the temperature control apparatus 100. To reduce the thermal inertia of the temperature control system 10 utilizes a two-channel approach with cold (e.g. room temperature) and hot air (e.g. heater stabilized at 60° C.) channels/lines. The air in the channels/lines may be mixed close to the animal in a turbulent flow chamber and delivered using hollow donut air injector located above the animal (see for example, FIGS. 6A and 7).

Referring to FIG. 2, the temperature control apparatus 100 includes a cooling fan 102 operatively connected to a cooling air line, a heating fan 104 operatively connected to a heating air line, a heating block 106 operatively connected to the heating fan 104 and the heating air line to heat the air within the heating air line, and a housing 105.

Figure 5A:
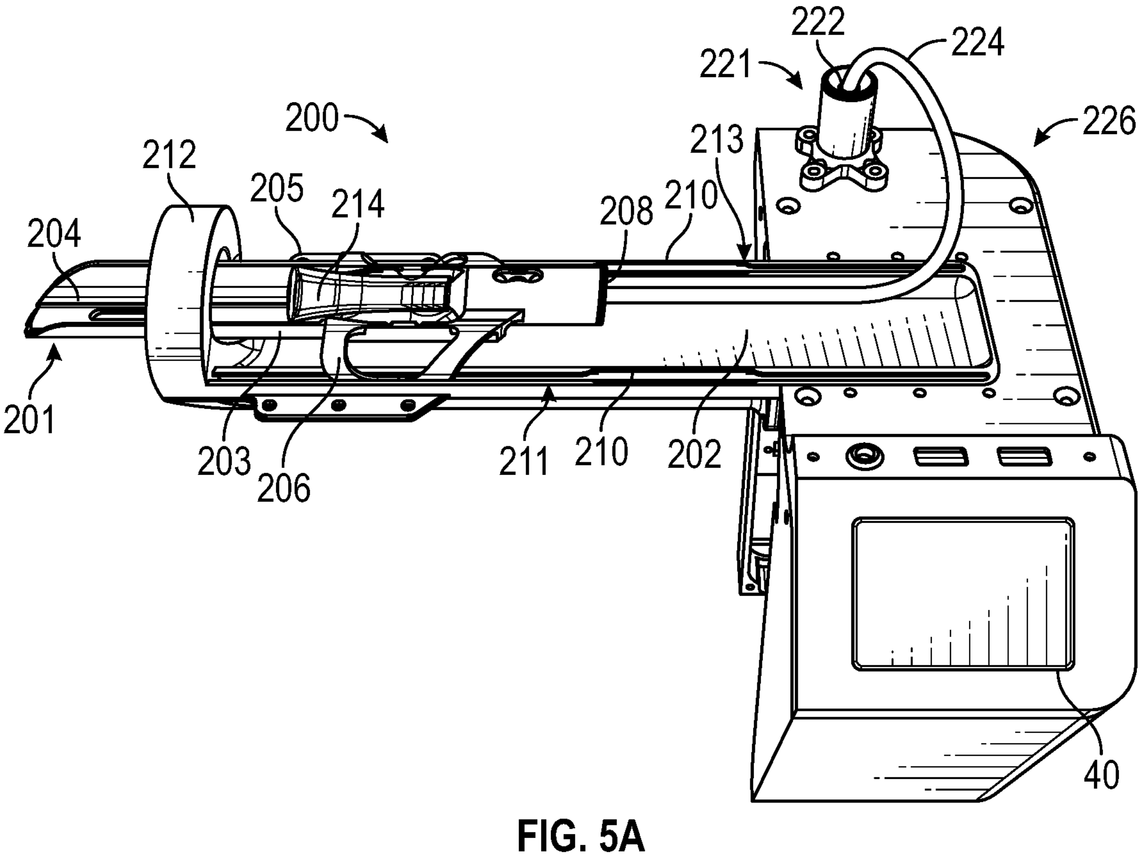
FIG. 5A, FIG. 5B, FIG. 5C, FIG. 5D, and FIG. 5E show an animal bed apparatus and temperature control system in an example.
Figure 5B:
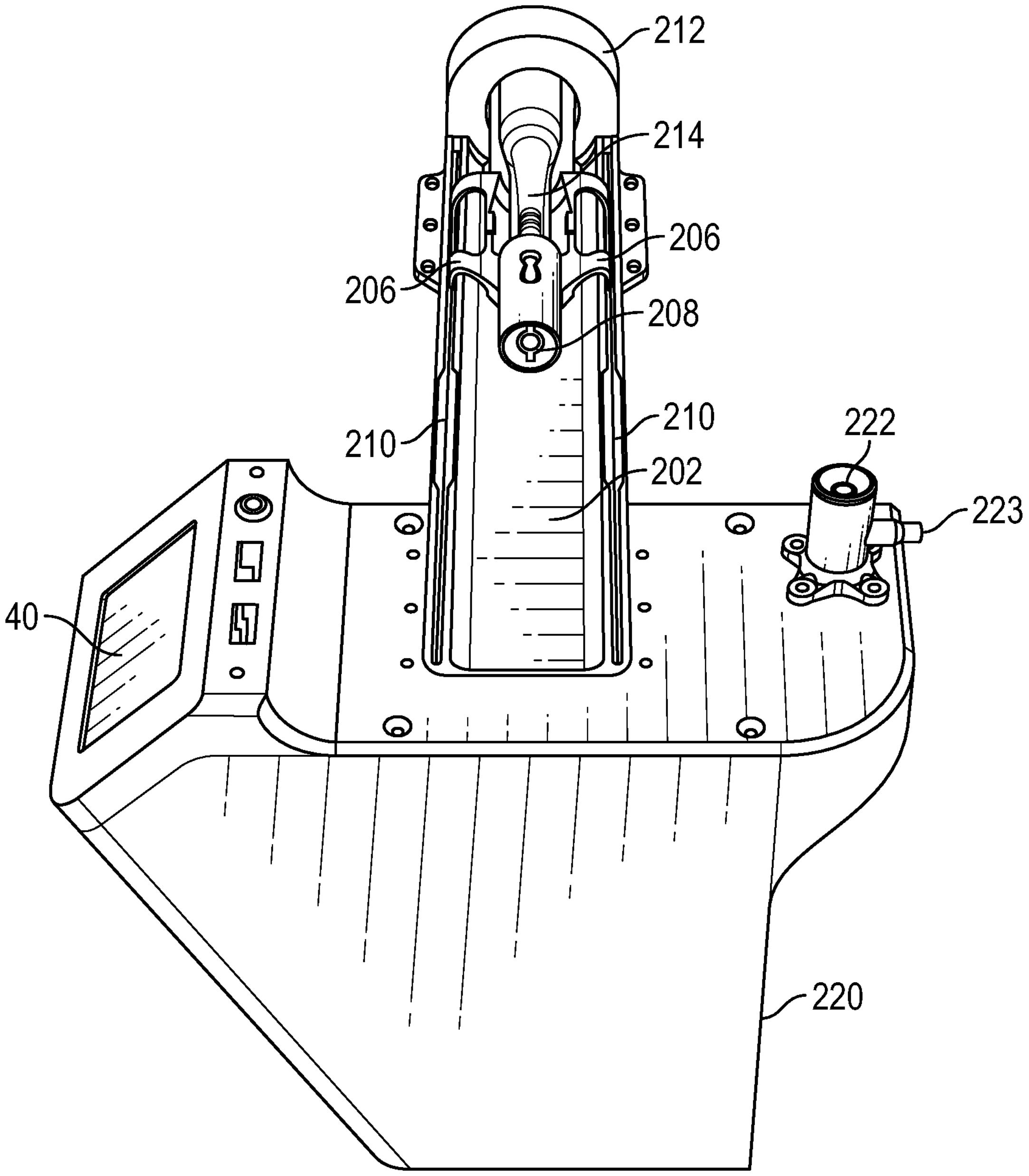
Figure 5C:
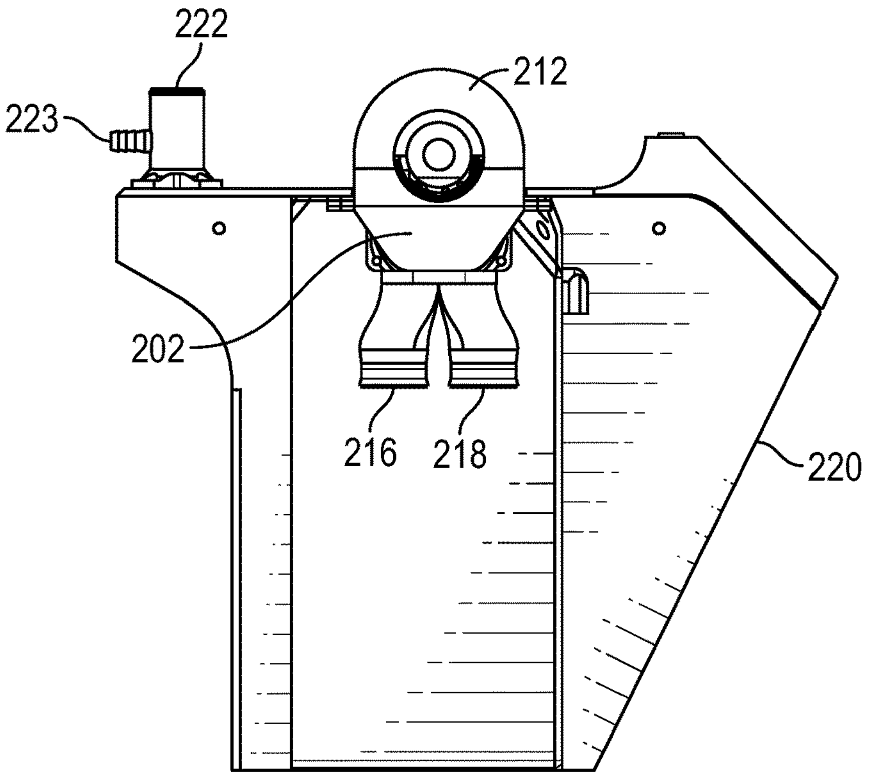

The cooling fan 102, heating fan 104, and heating block 106 are each located within the housing 105. In an embodiment, the cooling fan 102, heating fan 104, and heating block 106 may instead be located within a tower 220, as seen in FIG. 5E. In this embodiment, the tower 220 may allow for direct connection to an animal bed without the need for additional tubing. In some examples, the cooling fan 102, the heating fan 104, and/or the heating block 106 may directly connect to the animal bed apparatus. In other examples, the heating air line and the cooling air line directly connect to the animal bed apparatus. The tower 220 may further include a display 40, a sensor hub 30, and a controller.

In some embodiments, the animal 20 needing temperature control from the temperature control apparatus 100 may be non-human. In some additional embodiments, the animal 20 may not be able to regulate its body temperature while under anesthesia for imaging, thus subjecting the animal to fluctuations in body temperature while imaging takes place. In some examples, the animal is a mouse or a rat.

The temperature control apparatus 100 includes a cooling fan 102 operatively connected to a cooling air line. The cooling fan 102 may be a turbine or a high-pressure fan. In some embodiments, a cooler, such as a thermoelectric cooler or Peltier cooler, may be connected to the cooling fan 102. In other embodiments, the cooling fan may receive room temperature air from outside the housing 105 via an air inlet 103. In some embodiments, the temperature of the air in the cooling line may be between about 10° C. and about 22° C. In some examples, the temperature of the air in the cooling line may range from about 10° C. to about 15° C., about 15° C. to about 18° C., about 17° C. to about 20° C., or about 20° C. to about 22° C. In some examples, the temperature of the air in the cooling air line may be room temperature. In other examples, the temperature of the air in the cooling air line is below room temperature if a Peltier thermoelectric cooler is attached. The temperature of the air in the colling air line may depend on how far the air is from the cooling fan, air intake, or cooling element, such as a Peltier cooler.

The temperature control apparatus 100 includes a heating fan 104 operatively connected to a heating air line and a heating block 106. The temperature control apparatus 100 includes a heating block 106 operatively connected to the heating fan 104 and the heating air line to heat the air within the heating air line. The temperature of the heating block 106 may range from about 50° C. to about 70° C. In some embodiments, the temperature of the air in the heating air line may be between about 35° C. to about 70° C., about 35° C. to about 50° C., or about 50° C. to about 70° C. The temperature of the air in the heating air line may depend on how far the air is from the heating block.

Figure 6A:
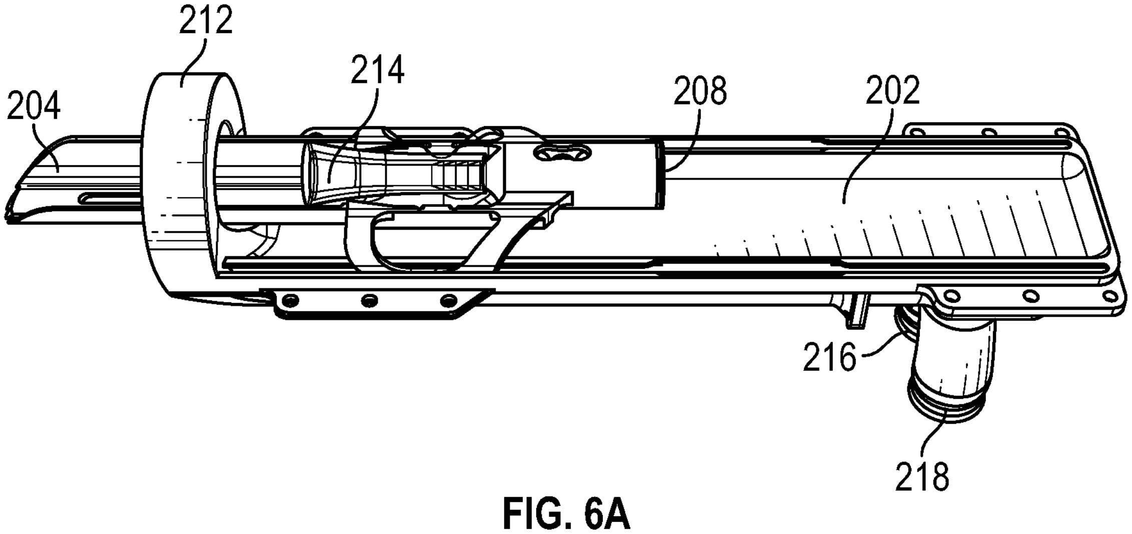
FIG. 6A is a side view of an animal bed in one example.
Figure 6B:
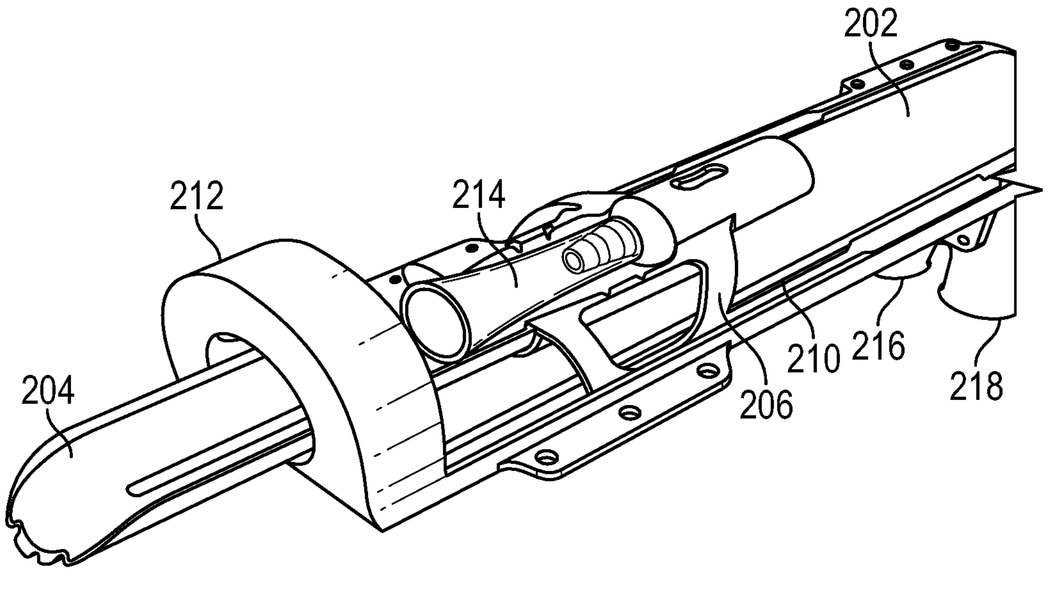
FIG. 6B is an isometric view of an animal bed in one example.

In some embodiments, the air in the cooling air line or in the heating air line may be atmospheric air or it may be purified air. The air from the heating air line and the air from the cooling air line may be combined. In some embodiments, the air may be combined as conditioned air outside of the temperature control apparatus. For example, as seen in FIGS. 6A and 7, the air from the heating air line and the air from the cooling air line may be combined within an animal bed apparatus with a turbulent flow chamber and delivered to the animal using an air injector located above the animal. In some embodiments, the temperature of the combination of the air in the cooling line and the air in the heating air line may be changed by adjusting parameters of the cooling fan 102, of the heating fan 104, and/or the heating block 106. In some additional embodiments, the temperature of the combination of the air in the cooling line and the air in the heating air line may change within minutes or seconds; that is, the temperature of the combination of the air in the cooling line and the air in the heating air line may change from a first temperature to a second temperature within minutes or within seconds. In some aspects, the temperature of the combination of the air in the cooling line and the air in the heating air line may change within about 10 seconds. In an example, the temperature of the combination of the air in the cooling line and the air in the heating air line may change in about 10 seconds per 5 degrees. In an embodiment, the controller is agile enough to response to animal heating by RD power. The change in the temperature of the combination of air may change the temperature of the animal within 30 seconds, within 1 minute, or within 2 minutes.

In some embodiments, the combination of the air from the cooling air line and air from the heating air line may be between about 32° C. to about 40° C., about 35° C. to 38° C., or about 37° C. to about 39° C. In an example, the optimal cooling and heating temperature is not above 40° C. to avoid potential skin damage. In at least one example, the temperature of the combination of the air is not below about 32° C., or is not less than 5° C. below average animal body temperature (e.g. 37° C.).

The temperature control apparatus 100 includes a housing 105. The fans/turbines 102/104, heating block 106, and controlled electronics (not shown) are housed in the housing 105. In an example, the housing 105 may be an aluminum enclosure outside of the magnet of an imaging system. In some embodiments, the housing 105 may further include an air inlet 103 operatively connected to the cooling fan 102 to introduce room temperature air into the cooling line. In some additional embodiments, the housing 105 may further include a cooling air line outlet 108 and a heating air line outlet 110 to connect the cooled or heated air in the respective cooling air line or heating air line to the animal bed apparatus. In an example, the outlets may be fabricated from PLA plastic. In some aspects, the cooling air line outlet 108 may include an indicator that air is flowing through the cooling air line. In some additional aspects, the heating air line outlet 110 may include an indicator that air is flowing through the heating air line. The indicator on either the cooling air line outlet or the heating air line outlet may be a light that surrounds the outlet or that projects from the outlet.

In some embodiments, the housing 105 is located in a tower. In an embodiment, the cooling fan 102, heating fan 104, and heating block 106 may instead be located within a tower 220, as seen in FIG. 5E. In this embodiment, the tower 220 may allow for direct connection to an animal bed apparatus without the need for additional tubing. The tower 220 may further include a display 40, a sensor hub 30, and a controller.

The temperature control apparatus 100 may further include a temperature control apparatus display 112. In some embodiments the temperature control apparatus display 112 is on the housing 105. In other embodiments, the temperature control apparatus display 112 is on the tower 220. The temperature control apparatus display 112 may be operable to display the temperature of the air in the cooling air line, the temperature of the air in the heating air line, and/or the temperature of the combination of the air in the cooling air line and the heating air line. In some examples, the temperature control apparatus display may be an OLED display.

The housing 105 of the temperature control apparatus 100 and/or the tower 220 may further include an on/off switch and a power input 116. The power input 116 may be operable to provide power to the cooling fan 102, the heating fan 104, the heating block 106, the controlled electronics (not shown), and/or the indicators for the cooling air line outlet 108 and the heating air line outlet 110.

Precise Magnetic Resonance Compatible Animal Control System

Further described herein is a system for heating or cooling an animal under anesthesia during imaging. In some embodiments, the animal may be non-human. In some additional embodiments, the animal may not be able to regulate its body temperature while under anesthesia for imaging, thus subjecting the animal to fluctuations in body temperature while imaging takes place. In some examples, the animal is a mouse or a rat.

The system is a precise magnetic resonance compatible animal temperature control system capable of fast reaction to changes in the animal environment. The system may be capable of maintaining precise animal temperature during an imaging session that includes active imaging periods and rest periods while the animal us under anesthesia. The cold channel can also be cooled with Peltier or thermoelectric cooling in cases when room temp cooling is not sufficient. This system may be encompassed along with an animal respiratory monitoring system making it a smart animal life support system for maintaining animal wellbeing during an imaging session. Other physiological parameters such as EKG etc. can be added to the system as needed.

The overall temperature control system 10 is shown in FIG. 1. The temperature control system 10 includes a temperature control apparatus 100 of the present disclosure, an air temperature sensor 36 operable to measure the temperature of a conditioned air flow from the cooling air line and the heating air line, an animal temperature sensor 34 operable to measure the temperature of the animal's body 20, and a sensor hub 30 in communication with the temperature control apparatus 100, air temperature sensor 36, and an animal temperature sensor 34.

Referring to FIG. 1, the temperature control system 10 may further include controller within the temperature control apparatus 100 and/or a display 40. In an embodiment, the temperature control apparatus 100, controller, sensor hub 30, and/or display 40 may be located within a tower 220, as seen in FIG. 5E. In an embodiment, the controller is a PID controller in the temperature control apparatus 100 and the sensor hub 30 supplies temperatures to the controller in the temperature control apparatus 100 for the purpose of control and to the display 40 for visualization. In some embodiments, the sensor hub 30 is responsible for acquiring temperatures of the animal and the conditioned air and communicating this information to the controller, the temperature control apparatus 100, and/or the display 40. In various aspects, the sensor hub 30 may include at least two thermocouple ports 32 for connecting the animal body temperature sensor 34 and the conditioned air temperature sensor 36. In addition, the sensor hub 30 may acquire a breathing trace from a respiratory pillow 38 and breathing sensor 37 via a breathing sensor port 39 and calculate breaths per minute. In some aspects, the sensor hub 30 may supply data to the controller, the display 40, or communicate the data to a host computer via USB.

The animal and heating air temperatures may be supplied from the sensor hub 30 to the display 40 and/or controller over a communication channel 50. For safety, if no measurements are supplied within 1 minute, the temperature control apparatus 100 may be shut down. In some embodiments, the communication channel 50 may be a I2C bus, Wi-Fi, or any other communication connection.

In some embodiments, the communication connection 60 between the sensor hub 30 and the temperature control apparatus 100 may be performed using a I2C bus, Wi-Fi, or any other communication connection. In an example, the sensor hub 30 may act as a server while the temperature control apparatus 100 may connect as a client. The sensor hub 30 and/or the controller of the temperature control apparatus 100 may be based on a microcontroller. In at least one example, the microcontroller may be an Adafruit ESP32 HUZZAH board with ESP32 microprocessor and have a built-in support I2C and Wi-Fi interfaces.

In some embodiments, the sensor hub 30 may include a multi-sensor high accuracy digital temperature measurement system connected to the controller using an SPI bus. For example, the temperature measurement system may have 24-bit high resolution ADC, allow at least 4 readings per second over up to 10 channels, and support a large variety of different sensors. In an embodiment, the sensor hub 30 may include at least two thermocouple ports 32 for connecting the animal body temperature sensor 34 and the conditioned air temperature sensor 36. In another embodiment, the sensor hub 30 may include a thermocouple input and a thermistor input.

In some embodiments, the conditioned air temperature sensor 36 may be a T-type thermocouple. Due to vicinity of the thermocouple to the source of RF radiation in the imager, the circuits may have reduced susceptibility to induced RF. For example, most of digital lines may include low pass filters.

The temperature control system 10 described herein includes an animal temperature sensor 34 operable to measure the temperature of the animal's body. The animal temperature sensor 34 is operable to communicate the temperature of the animal's body to the sensor hub and the controller. The animal temperature sensor may include a rectal thermometer, an oral thermometer, or an infrared thermometer. In some examples, the animal temperature sensor is a rectal thermometer.

In some embodiments, the system may further include a breathing sensor 37 operable to measure the breathing rate of the animal 20. In some aspects, the breathing sensor 37 may be a pressure sensor operable to detect when the animal inhales and exhales. In an example, the breathing sensor 37 is a differential pressure sensor coupled to a respiratory pillow 38. The pressure may be digitized from 100 to 25 times a second. The breathing sensor may be connected to the controller and the controller may be operable to calculate the animal's breathing rate using a peak detection algorithm. For example, the algorithm signals if a new datapoint is a given number of standard deviations away from the moving mean. The constructs a separate moving mean and deviation, such that new signals do not corrupt the calculated target.

Prior to imaging, a target temperature, a maximum air temperature, and/or a target temperature range of the animal may be determined. The target temperature may be within the target temperature range. The target temperature range may be the range of body temperatures for a small animal under anesthesia undergoing imaging to prevent hypothermia due to anesthesia and RF heating due to imaging. In some embodiments the target temperature range may be from about 32° C. to about 40° C., about 35° C. to 38° C., or about 37° C. to about 39° C. The target temperature may be 35° C.±0.5° C., 36° C.±0.5° C., 37° C.±0.5° C., 38° C.±0.5° C., or 39° C.±0.5° C. In some embodiments, the target temperature may vary based upon several factors, such as the size of the animal or the species of the animal.

The controller is operable to monitor the temperature of the conditioned air flow to the animal and the temperature of the animal's body. The controller may be operable to control the temperature control apparatus with a cooling air line (e.g. room temp) and a heating air line that can control the animal's temperature precisely with a fast reaction time of a few minutes. When the temperature of the animal falls outside of the target temperature range, the temperature of the animal needs to be corrected. In some embodiments, the controller may be operable to automatically adjust the temperature of the conditioned air flow to correct the temperature of the animal.

In an embodiment, the controller may be operable to automatically maintain the animal's temperature within the target temperature range for a portion of or the duration of the imaging session. In some embodiments, the controller may be operable to automatically maintain the animal's target temperature within 0.5° C., 1° C., or 2° C. for 1 minute, 2 minutes, 5 minutes, 10 minutes, 30 minutes, or the duration of the imaging session. For example, the temperature control system may maintain an animal target temperature of 35° C.±0.5° C., 36° C.±0.5° C., 37° C.±0.5° C., 38° C.±0.5° C., or 39° C.±0.5° C. for 1 minute, 2 minutes, 5 minutes, 10 minutes, 30 minutes, or the duration of the imaging session.

In some aspects, the controller may be a proportional (P) controller, a proportional-integral controller (PI), a proportional-integral-derivative controller (PID), or a double loop PID controller operable to automatically adjust the temperature of the conditioned air flow. In some examples, the controller is a double loop PID controller operable to automatically adjust the temperature of the conditioned airflow.

In an example, a first PID loop may monitor the temperature of the animal and supply a second PID loop with a target temperature. The second PID loop may monitor temperature at an exhaust of the temperature control system and control the composition of the conditioned air by changing the flow of the heating or cooling fans/turbines. To prevent cooling of the heating lines, a minimum flow of about 15% may constantly be supplied through the heating line/channel.

In various embodiments, the controller is operable to predict what it has to do to get to a setpoint (e.g. target temperature range) and automatically adjust elements in the system to obtain and maintain the setpoint. In some embodiments, the controller comprises a plurality of PID controllers. In at least one embodiment, the controller may comprise three PID controllers. For example, a first PID controller (main controller) may be operable to set the temperature of the conditioned air flow the to the value appropriate for conditioning animal temperature (SP=target animal temperature, PV is animal temperature, CV=desired mixture temperature). A second PID controller (air mixture controller) may be operable to set the air flow of the cold air line of the temperature control apparatus to maintain gas mixture temperature as set by the first PID controller (SP=target conditioned air temperature, PV is measured conditioned air temperature, CV=flow of the cooling fan). A third PID controller (heating block controller) may be operable to control the duty cycle of the heating block to maintain its temperature constant (SP=desired heating block temperature, PV is the heating block temperature, CV=duty cycle of the heating block (percent of power delivered to heating block). In some examples, the third PID controller is operable to turn the heating block and/or the heating fan on and off.

In some embodiments, the controller may have a modular design to utilize different heating and visualization configurations or use the same temperature control apparatus/system with different sensor hubs located at the imaging system, transportation cart, or preparation room.

In some embodiments, the controller adjusts a setting of the cooling fan, the heating fan, and/or the heating block to adjust the temperature of the conditioned air flow. In some aspects, the setting may include the speed of the cooling fan, the speed of the heating fan, or the temperature of the heating block. For example, the controller may adjust the flow rate of the heating fan to be about 100 to 120 out of 255 (0—no flow, 255 max flow, not linear). In another example, the controller may adjust the flow rate of the cooling fan to about 0 to 255 out of 255 (0—no flow, 255 max flow, not linear). In some additional aspects, the heating fan speed may be kept constant to keep the heating block temperature stable. In some embodiments, the controller may be in communication with a server to log data related to the measured temperatures and the adjustments made to the settings of the cooling fan, the heating fan, and/or the heating block.

In some embodiments, the speed of the cooling fan may be adjusted to adjust the temperature of the conditioned air flow. In some aspects, the temperature of the air in the cooling air line may be between about 12° C. to about 22° C. In some embodiments, the air in the cooling air line or in the heating air line may be atmospheric air or it may be purified air. In some examples, the temperature of the air in the cooling air line may be room temperature. In other examples, the temperature of the air in the cooling air line may be below room temperature if a Peltier thermoelectric cooler is attached.

In some embodiments, the speed of the heating fan is adjusted to adjust the temperature of the conditioned air flow. In some aspects, the temperature of the air in the heating air line may be between about 35° C. to about 50° C. In some embodiments, the heating fan may continuously operate to provide a minimum flow rate of hot air to prevent the heating air line from cooling. In some examples, the minimum flow rate of the air in the heating air line may be about 15% of the maximum flow rate of the air in the heating air line.

In some aspects, the temperature of the conditioned air flow may be between about 32° C. to about 40° C. The temperature of the conditioned air flow may be adjusted related to the target temperature range. The temperature of the conditioned air flow may be adjusted to be higher (i.e., warmer) than the target temperature range to prevent hypothermia caused by anesthesia. The temperature of the conditioned air flow may be adjusted to be lower (i.e., cooler) than the target temperature range to prevent overheating caused by RF heating due to imaging. For example, the PID controller is a continuous mode controller operable to reduce heating for a temperature above the target and increase heating for a temperature below the target.

In some embodiments, the temperature of the heating block is adjusted to adjust the temperature of the conditioned air flow. In some aspects, the temperature of the heating block may be between about 50° C. to about 70° C. In some additional aspects, the temperature of the heating block may be constant during imaging. In some examples, the temperature of the heating block may be about 60° C. for the duration of imaging. For very short distance from temperature control apparatus to animal bed apparatus, lower temperatures may be used (e.g. 55° C.), and when the temperature control apparatus is located further away, higher temperatures may be used to compensate heat losses during transportation.

In some embodiments, the conditioned air flow may have a relative humidity of between about 30% and about 100%, or between about 30% and 50%. The moisture content of the conditioned air flow may be measured with a hygrometer. The hygrometer may be operatively connected to the controller.

In some embodiments, the system may further include additional physiological monitors to measure one or more physiological parameters. In some examples, the additional physiological monitors may include heart rate monitors, blood pressure monitors, oxygen saturation monitors, EKG, or pulse monitors.

In some embodiments, the display 40 and/or the temperature control apparatus display 112 may be operable to communicate to the controller. In some additional aspects, the display 40 may be operable to display to the temperature of the conditioned air flow, the temperature of the air in the cooling air line, the temperature of the air in the heating air line, the moisture content of the conditioned air flow, or the temperature of the animal. The display 40 may be operable to receive inputs from a user. For example, a user may enter information about the animal, a target temperature, or other information about the animal, the temperature, and/or the imaging session. In some embodiments, the system may further include a tower, where the display is located on a surface of the tower and the sensor hub and/or the controller is located within the tower. In some additional embodiments, when the system includes additional physiological monitors, the display may be operable to display data related to the one or more physiological parameters measured by the physiological monitors. In some examples, the display is an OLED display.

In some embodiments, the system may further include an animal ID reader in communication with the controller. The animal ID reader may be operable to read a bar code, a radio frequency identification (RFID) tag, or a quick response (QR) code. The animal ID may include identifying information about the animal.

Bed and Rail System

Described herein is an animal bed apparatus for use in an imaging apparatus and system, as seen in FIGS. 5A-7. In some embodiments, the animal in need of imaging may be a non-human animal. In some aspects, the non-human animal may be a mouse or a rat.

The animal bed apparatus 200 includes an animal bed 201 that includes a support surface 204 having a first longitudinal side 203 and a second longitudinal side 205. The support surface 204 is operable to hold an animal and may have a generally curved shape to support the animal. The support surface has a pair of rails 206 along at least a portion of the first longitudinal side 203 and the second longitudinal side 205. The animal bed 201 further includes a mask 214 that may extend along a portion of the support surface 204, as seen in FIG. 5A. The mask 214 is operable to hold anesthesia over the animal when the animal is on the support surface 204. The animal bed 201 further includes an anesthesia inlet 208 operably connected to the mask 214 and operable to be connected to an anesthesia source via an anesthesia line (not shown). The anesthesia line may be flexible tubing. In some embodiments, the anesthesia source may be directly connected to the anesthesia inlet and thus there is no connection line between them.

The apparatus 200 further includes a base 202, which includes rail slots 210 along a first longitudinal edge 211 and a second longitudinal edge 213. The rail 206 on the portion of the first longitudinal side 203 of the animal bed support surface 204 is operable to slide within the rail slot 210 along the first longitudinal edge 211 of the base 202 and the rail 206 on the portion of the second longitudinal side 205 of the animal bed support surface 204 is operable to slide within the rail slot 210 along the second longitudinal edge 213 of the base 202.

The apparatus 200 further includes an air injector 212 connected to or incorporated into the base 202. The air injector 212 is operable to blow conditioned air over the animal on the animal bed 201. The air injector 212 may include an opening such that the animal bed can slide through the opening of the air injector. The opening also allows air to be directed to a greater surface area of the animal and of the bed. In some embodiments, the air injector may be circular, ovular, elliptical, triangular, rectangular, pentagonal, hexagonal, or octagonal in shape. For example, the air injector 212 may have a "donut" shape.

Referring to FIGS. 50, 6A-6B, and 7A-7B, the base 202 may further include a cooling air line inlet 216 operable to connect to a cooling air line and/or a heating air line inlet 218 operable to connect to a heating air line from a temperature control apparatus 100, such as a temperature control apparatus of the present disclosure.

Figure 7A:
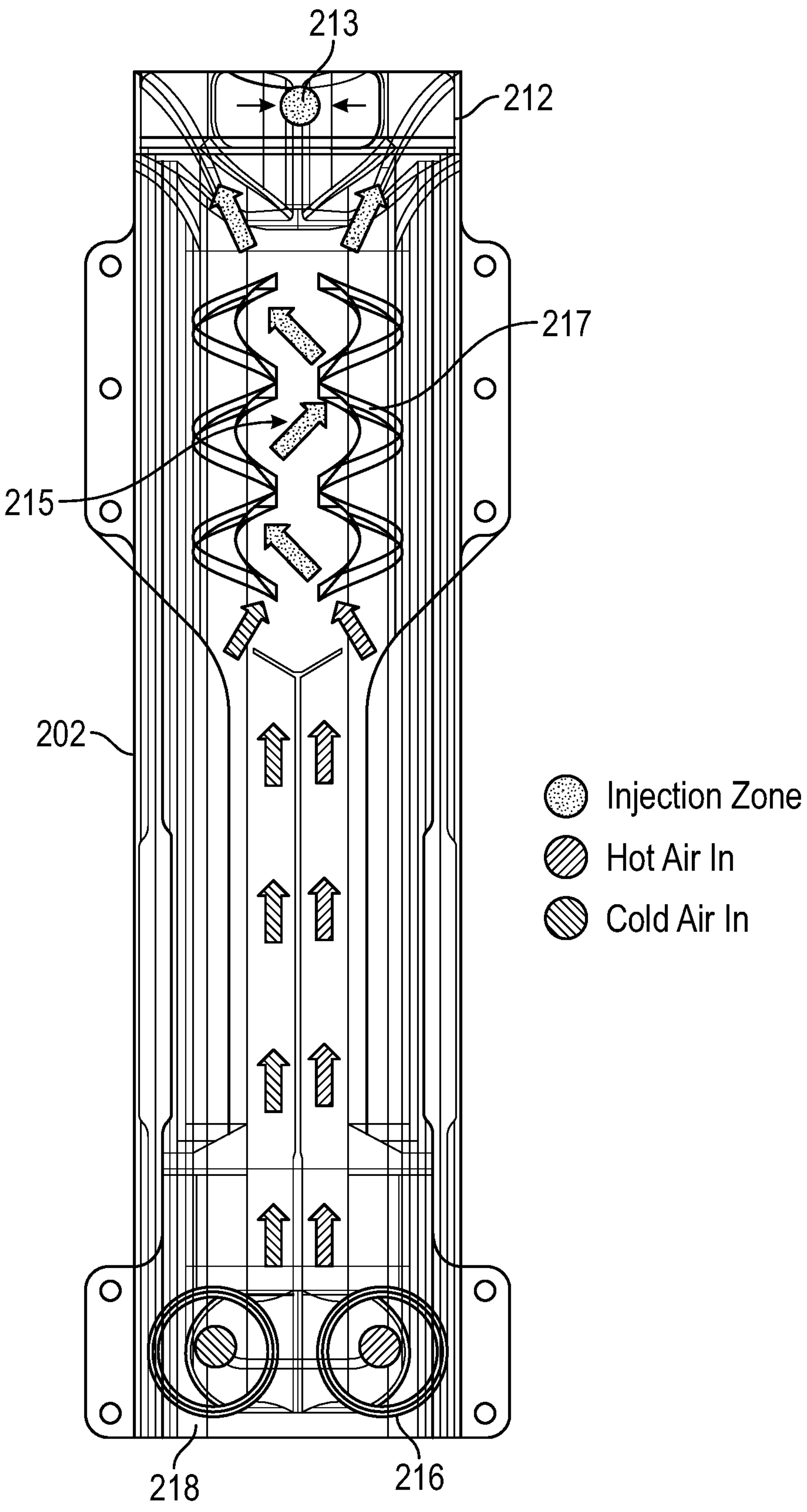
FIG. 7A shows the mixing area and injection zone within the body of the animal bed.

In some embodiments, the base 202 may further include an injection zone 213 operable to combine air from the cooling air line and the heating air line. The combined air from the cooling air line and the heating air line creates conditioned air that is blown over the animal at the air injector. In some aspects, as seen in FIG. 7A, the mixing area 215 of the base 202 may include one or more baffles 217 that facilitate combining the air form the cooling air line and the heating air line to form the conditioned air that exits through the injection zone 213 of the air injector 212.

Figure 7B:
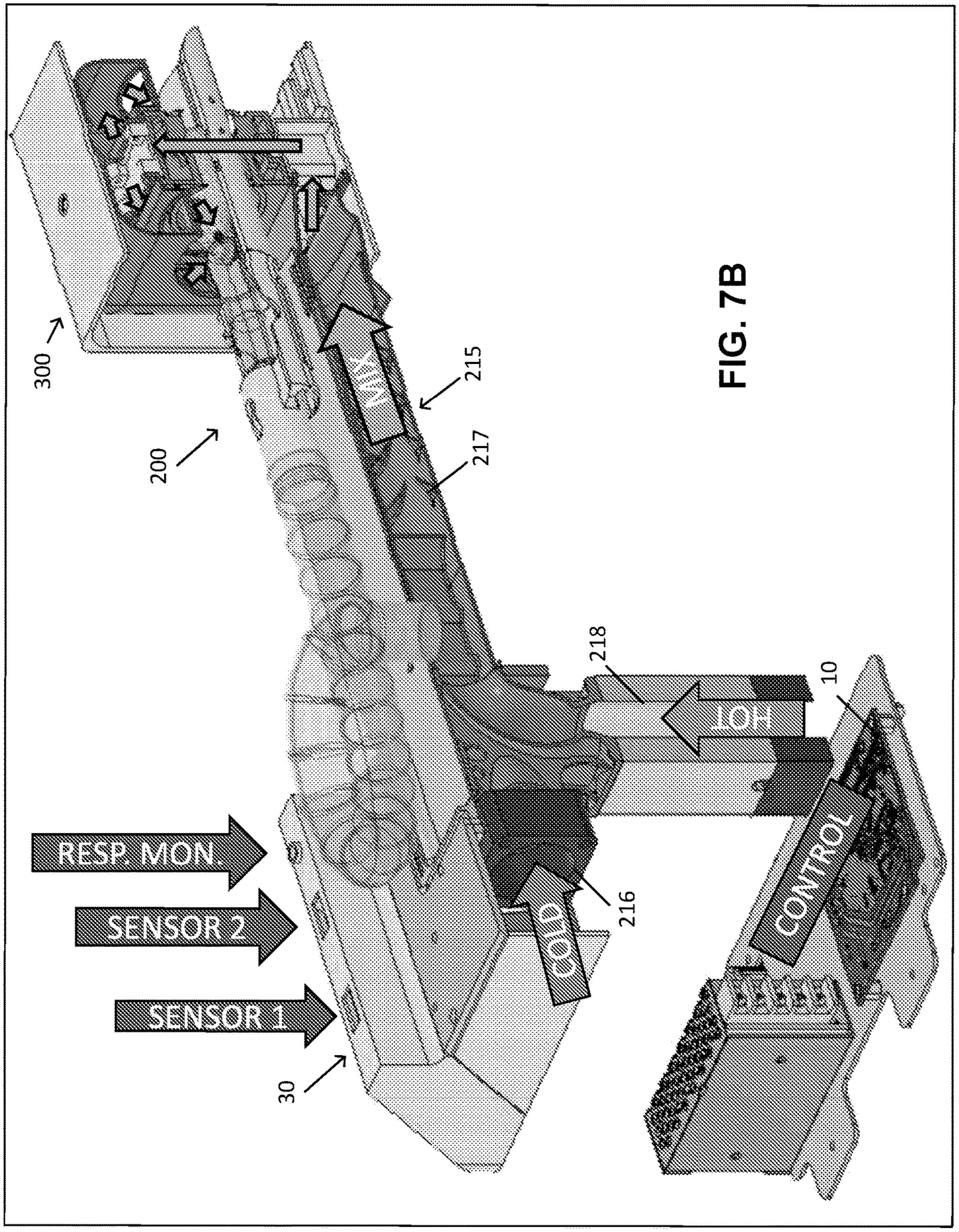
FIG. 7B shows a cross-section of a hollow resonator connected to an animal bed with a mixing area within the body.

Referring to FIG. 7B, the mixing area 215 of the base 202 may include one or more baffles 217 that facilitate combining the air form the cooling air line and the heating air line to form the conditioned air. In this aspect, the conditioned air may enter the body of the resonator of the imaging system 300 without an air injector. Instead, a hollowed resonator may evenly distribute the conditioned air around the animal, as the resonator serves as air duct. The conditioned air may move throughout the body of the resonator and may circulate naturally within the open spaces of the resonator. In some examples, the resonator may include a fan to aid in distributing the conditioned air. FIG. 7B shows an example air path of the conditioned air moving around the resonator body and therefore around the animal. In this example, because the resonator acts as an air duct, the temperature of the air around the animal may be more evenly distributed and may provide a consistent temperature within the body of the resonator.

Figure 8A:
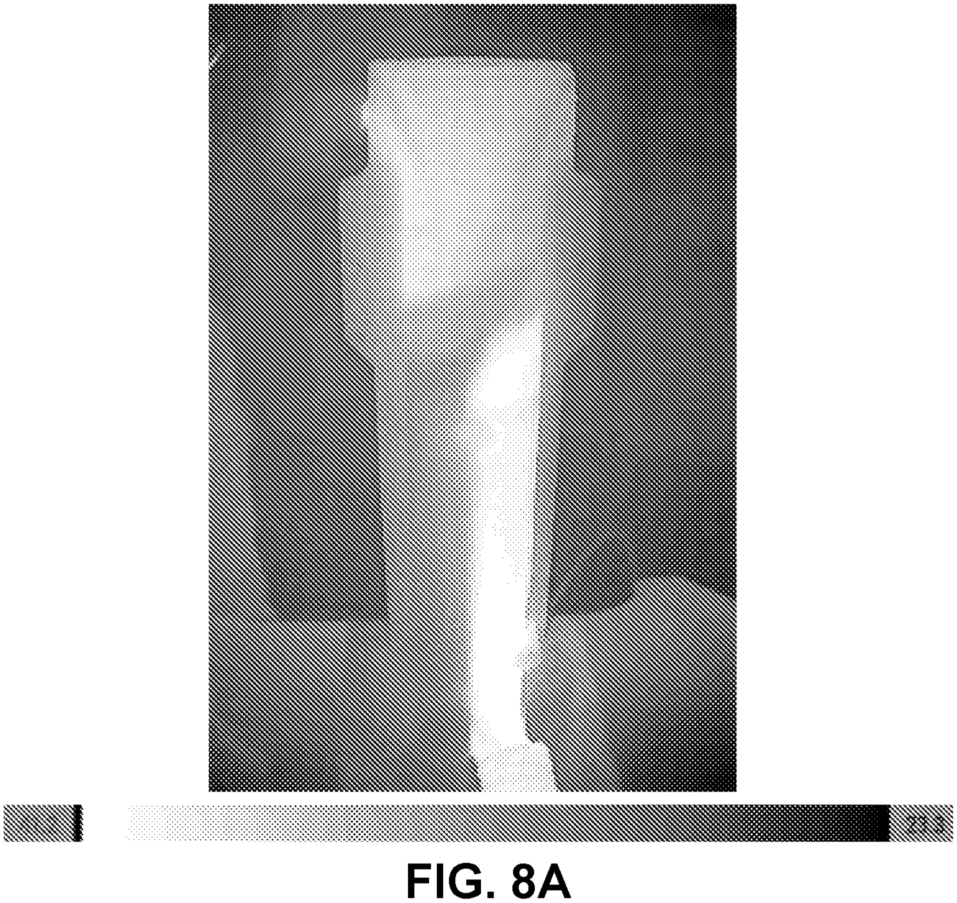
FIG. 8A shows the mixing of the combined air within the mixing area and the injection zone in one example.
Figure 8B:
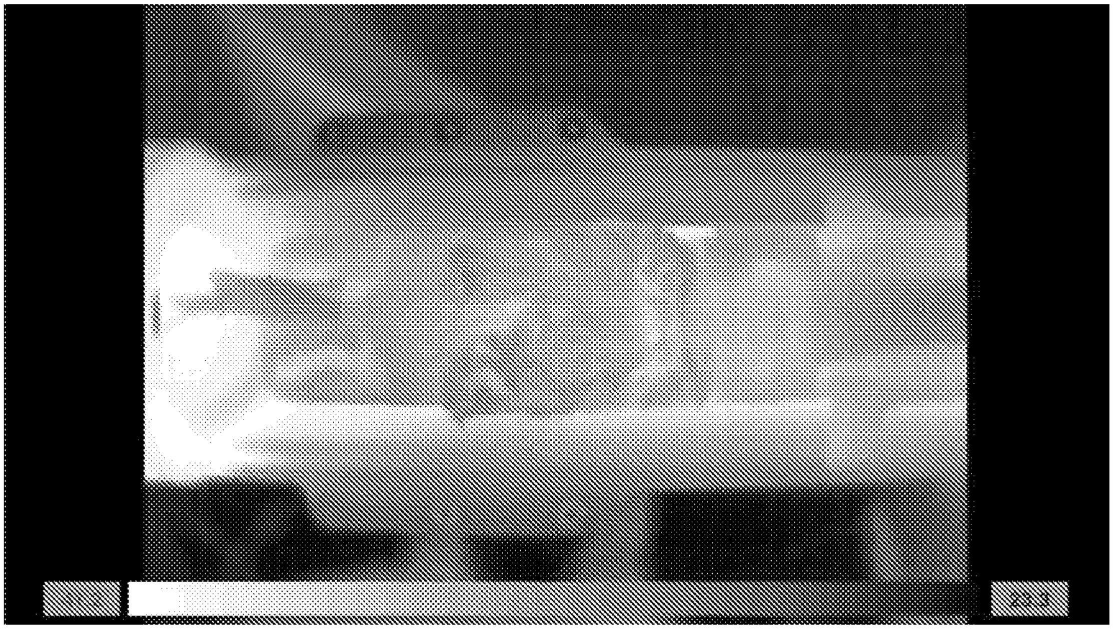
FIG. 8B is an animal heat map that shows homogenous animal heat distribution in one example.

In an example, FIG. 8A shows the mixing of the combined air within the mixing area 215 and FIG. 8B is an animal heat map that shows homogenous animal heat distribution.

In some embodiments, the animal bed apparatus 200 may further be operable to connect to and/or hold a temperature sensor operable to measure a temperature of the animal, an air temperature sensor operable to measure a temperature of the conditioned air, and/or include a breathing sensor (i.e. respiratory monitor) operable to measure the breathing rate of the animal. In some aspects, the temperature sensor may include a rectal thermometer, an oral thermometer, or an infrared thermometer. In some aspects, the breathing sensor may be a pressure sensor operable to detect when the animal inhales and exhales. In some examples, the breathing sensor is a differential pressure sensor connected to a respiratory pillow.

In some embodiments, the animal bed apparatus may further include a controller. In some aspects, the controller may be operable to control the location of the animal bed along the base. In some additional aspects, the controller may be the controller within the temperature control system disclosed herein. In yet additional aspects, the controller may be operable to control delivery of anesthesia to the animal. In some examples, the controller may be located within the support surface, the sensor hub, or the tower. In an example, the controller may be the controller of the temperature control system 10.

In some embodiments, the animal bed apparatus 200 may further include a display. The display may be in communication with the controller. In some aspects, the display may be operable to display the temperature of the animal. In some additional aspects, the display may be operable to display the breathing rate of the animal. In some examples, the display is the display 40.

Figure 6C:
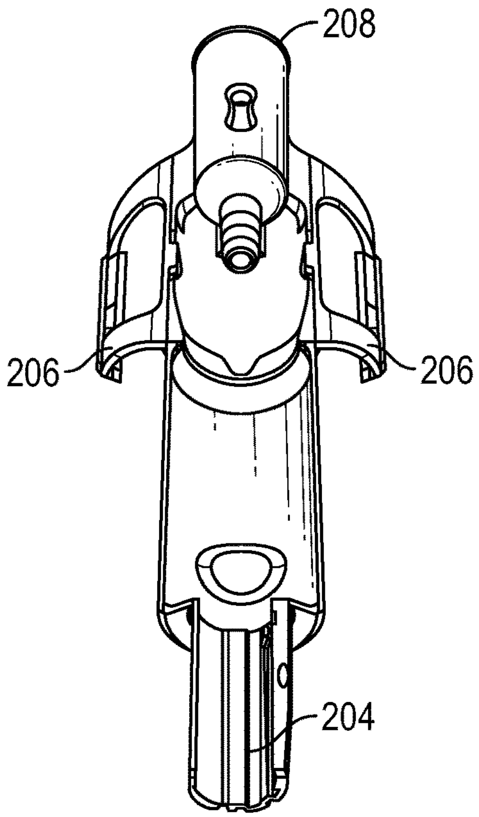
FIG. 6C is an animal bed for imaging a limb of an animal in one example.
Figure 6D:
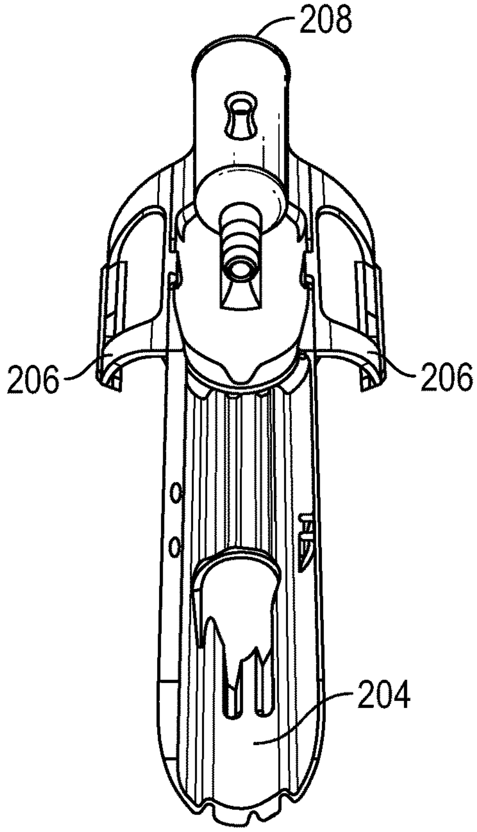
FIG. 6D is an animal bed for imaging the whole body of an animal in one example.

In some embodiments, the animal bed apparatus may be sized to facilitate imaging a limb of the mouse or rat. FIG. 6C shows an animal bed with a support surface 204 sized to support an animal limb to be imaged. In some examples, the support surface 204 may be amount 19 mm in length. In some additional embodiments, the animal bed apparatus may be sized to facilitate imaging of the whole body of the mouse or the rat. FIG. 6D shows an animal bed with a support surface 204 sized to support the whole body of the animal. The animal bed apparatus may about 200 mm to 250 mm in length. In some examples, the support surface 204 may be about 32 mm to about 115 mm in length.

Figure 5D:
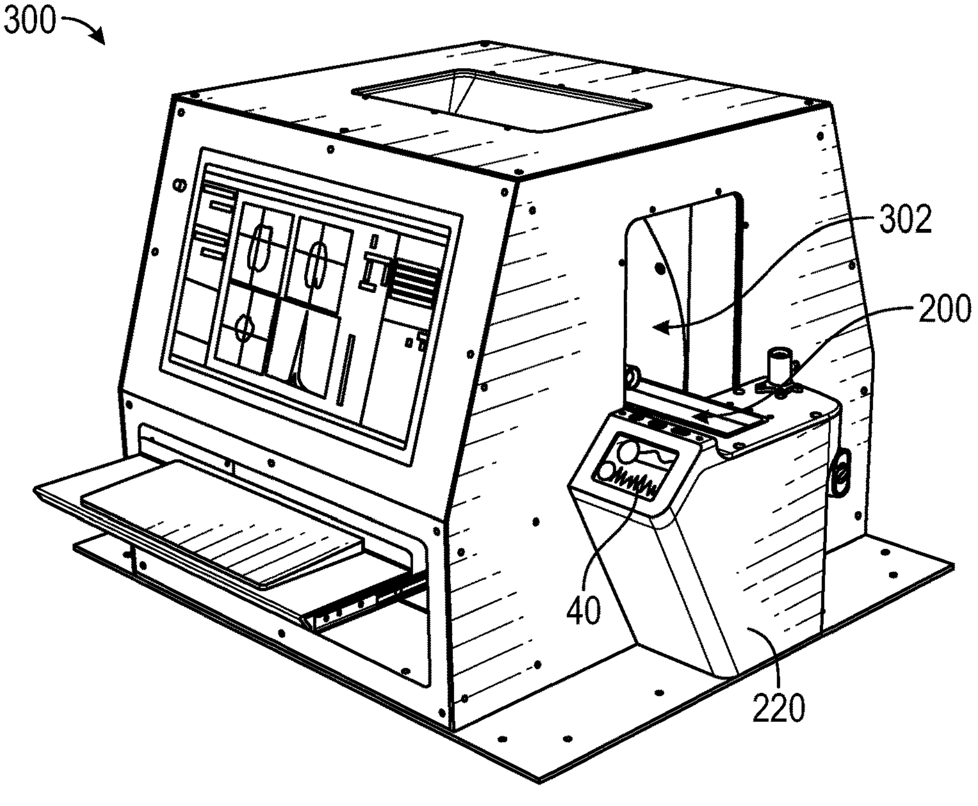
Figure 5E:
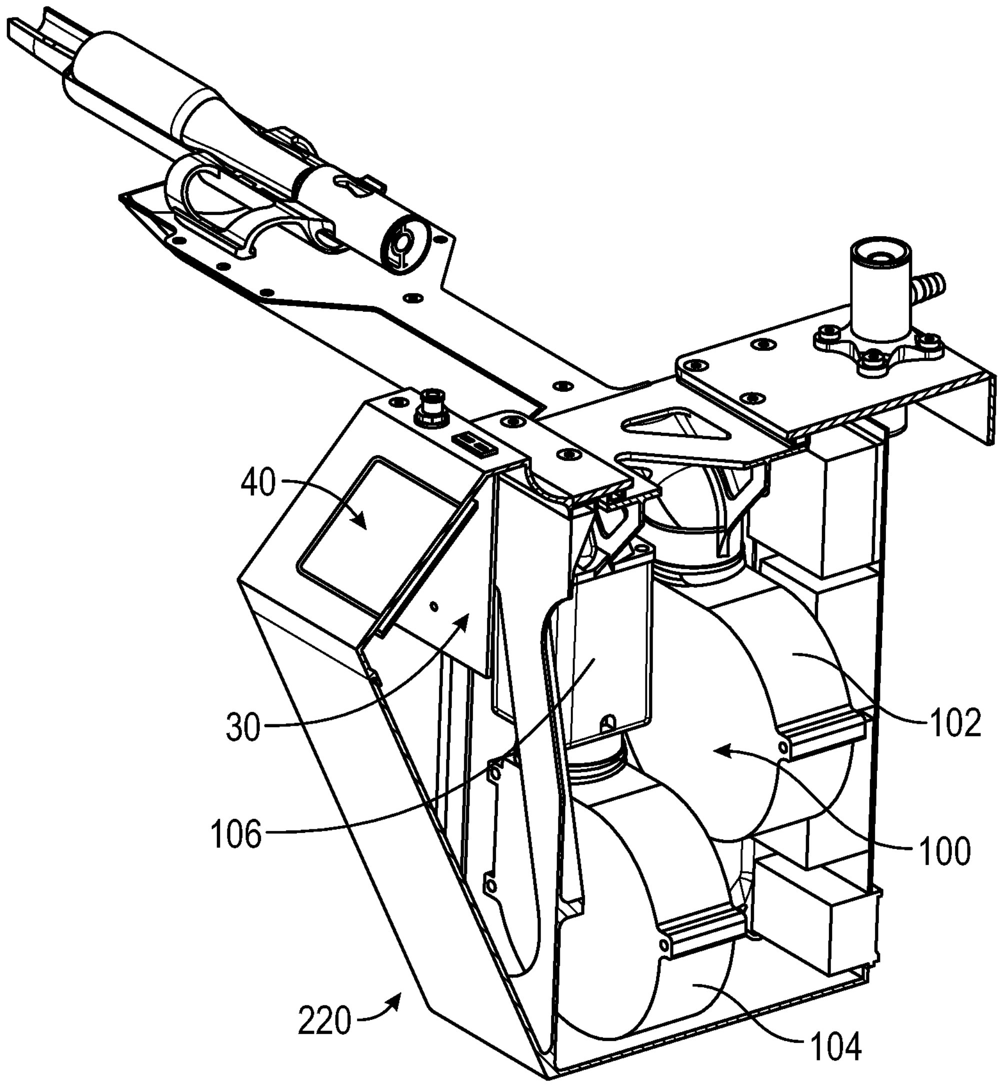

In some embodiments, the animal bed apparatus 200 may further include a tower 220 connected to the base 202 to facilitate proper positioning of the animal bed 201 and base 202 within an imaging system 300, seen in FIG. 5D. In some examples, the display 40 may be located on a surface of the tower 220, as seen in FIGS. 5A, 5B, 5D, and 5E.

In some aspects, the tower 220 may include an anesthesia splitter 221. The anesthesia splitter 221 may include a supply line inlet 223, an anesthesia outlet 222, and an exhaust outlet (not shown). The supply line inlet 223 may be connected to an anesthesia source the via a supply line. The supply line inlet 223 may be fluidly connected to the anesthesia outlet 222 through the anesthesia splitter 221. The anesthesia outlet 222 may be connected to the anesthesia inlet 208 on the animal bed 201 via an anesthesia line 224. In some examples, the supply line and/or the anesthesia line 224 may be a flexible hose.

In an embodiment, the temperature control apparatus 100 may be located within the tower 220, as seen in FIG. 5E. The cooling air line and heating air line of the temperature control apparatus 100 may then be operable to directly connect to the animal bed apparatus. In some examples, the cooling fan 102, the heating fan 104, and/or the heating block 106 may directly connect to the animal bed apparatus.

Smart Ecosystem with Animal Bed

Described further herein is an animal bed system 400 for maintaining an animal's temperature while being imaged under anesthesia. In some embodiments, the animal may be a non-human animal. In some aspects, the animal may not be able to regulate its body temperature while under anesthesia for imaging, thus subjecting the animal to fluctuations in body temperature while imaging takes place. In some examples, the non-human animal may be a mouse or a rat.

The system 400 includes a temperature control apparatus 100 of the present disclosure and an animal bed apparatus 200 of the present disclosure operable to hold an animal. The animal bed system 400 includes an air temperature sensor 36 operable to measure the temperature of the conditioned air flow from the air injector 212. The animal bed system 400 includes an animal temperature sensor 34 operable to measure the temperature of the animal's body. The animal bed system 400 further includes a controller in communication with the temperature control apparatus 100, air temperature sensor 36, and the animal temperature sensor 34. The controller is operable to monitor the temperature of the conditioned air flow to the animal and the temperature of the animal's body.

In some examples, the controller is within a sensor hub 30. In some embodiments, referring back to FIG. 1, the sensor hub 30 may be operable to connect to the animal temperature sensor 34, the air temperature sensor 36, a breathing sensor 37, the temperature control apparatus 100, a display 40, and the controller. In various aspects, the sensor hub 30 may include at least two thermocouple ports 32 for connecting the animal body temperature sensor 34 and the conditioned air temperature sensor 36. In addition, the sensor hub 30 may acquire a breathing trace from a respiratory pillow 38 and breathing sensor 37 via a breathing sensor port 39 and calculate breaths per minute. In some aspects, the sensor hub 30 may supply data to the controller, the display 40, or communicate the data to a host computer via USB.

The animal and heating air temperatures may be supplied from the sensor hub 30 to the display 40 and/or controller over a communication channel 50. For safety, if no measurements are supplied within 1 minute, the temperature control apparatus 100 may be shut down. In some embodiments, the communication channel 50 may be a 12C bus, Wi-Fi, or any other communication connection.

In some embodiments, the communication connection 60 between the sensor hub 30 and the temperature control apparatus 100 may be performed using a I2C bus, Wi-Fi, or any other communication connection. In an example, the sensor hub 30 may act as a server while the temperature control apparatus 100 may connect as a client. The sensor hub 30 and the temperature control apparatus 100 may be based on a microcontroller, for example the Adafruit ESP32 HUZZAH board with ESP32 microprocessor and have a built-in support I2C and Wi-Fi interfaces, in one example.

In some embodiments, the sensor hub 30 may include a multi-sensor high accuracy digital temperature measurement system connected to the controller using an SPI bus. For example, the temperature measurement system may have 24-bit high resolution ADC, allow at least 4 readings per second over up to 10 channels, and support a large variety of different sensors. In an embodiment, the sensor hub 30 may include at least two thermocouple ports 32 for connecting the animal body temperature sensor 34 and the conditioned air temperature sensor 36. In another embodiment, the sensor hub 30 may include a thermocouple input and a thermistor input.

In some embodiments, the conditioned air temperature sensor 36 may be a T-type thermocouple. Due to vicinity of the thermocouple to the source of RF radiation in the imager, the circuits may have reduced susceptibility to induced RF. For example, most of digital lines may include low pass filters.

The animal temperature sensor 34 is operable to measure the temperature of the animal's body. The animal temperature sensor 34 is operable to communicate the temperature of the animal's body to the sensor hub 30 and the controller. The animal temperature sensor may include a rectal thermometer, an oral thermometer, or an infrared thermometer. In some examples, the animal temperature sensor is a rectal thermometer.

In some embodiments, the system 400 may further include a breathing sensor 37 operable to measure the breathing rate of the animal 20. In some aspects, the breathing sensor 37 may be a pressure sensor operable to detect when the animal inhales and exhales. In an example, the breathing sensor 37 is a differential pressure sensor coupled to a respiratory pillow 38. The pressure may be digitized from about 25 to about 100 times a second. In one example, the pressure may be digitized about 40 times a second. The breathing sensor 37 may be connected to the controller and the controller may be operable to calculate the animal's breathing rate using a peak detection algorithm. For example, the algorithm signals if a new datapoint is a given number of standard deviations away from the moving mean. The constructs a separate moving mean and deviation, such that new signals do not corrupt the calculated target.

Prior to imaging, a target temperature and/or a target temperature range may be determined. The target temperature may be within the target temperature range. The target temperature range may be for a small animal under anesthesia undergoing imaging to prevent hypothermia due to anesthesia and RF heating due to imaging. In some embodiments the target temperature range may be from about 32° C. to about 40° C. In one example, the target temperature range is about 36° C. to about 37° C., about 35° C. to 38° C., or about 37° C. to about 39° C. The target temperature may be 35° C.±0.5° C., 36° C.±0.5° C., 37° C.±0.5° C., 38° C.±0.5° C., or 39° C.±0.5° C. In some embodiments, the target temperature may vary based upon several factors, such as the size of the animal or the species of the animal.

The controller is operable to monitor the temperature of the conditioned air flow to the animal and the temperature of the animal's body. When the temperature of the animal falls outside of the target temperature range, the temperature of the animal needs to be corrected. In some embodiments, the controller may be operable to adjust the temperature of the conditioned air flow to correct the temperature of the animal.

In an embodiment, the controller may be operable to automatically maintain the animal's temperature within the target temperature range for a portion of or the duration of the imaging session. In some embodiments, the controller may be operable to automatically maintain the animal's target temperature within 0.5° C., 1° C., or 2° C. for 1 minute, 2 minutes, 5 minutes, 10 minutes, 30 minutes, or the duration of the imaging session. For example, the temperature control system may maintain an animal target temperature of 35° C.±0.5° C., 36° C.±0.5° C., 37° C.±0.5° C., 38° C.±0.5° C., or 39° C.±0.5° C. for 1 minute, 2 minutes, 5 minutes, 10 minutes, 30 minutes, or the duration of the imaging session.

In some aspects, the controller may be a P controller, a PI controller, a PID controller, or a double loop PID controller operable to automatically adjust the temperature of the conditioned air flow. In some examples, the controller is a double loop PID controller operable to automatically adjust the temperature of the conditioned air flow.

In an example, a first PID loop may monitor the temperature of the animal and supply a second PID loop with a target temperature. The second PID loop may monitor temperature at an exhaust of the temperature control system and control the composition of the conditioned air by changing the flow of the heating or cooling fans/turbines. To prevent cooling of the heating lines, a minimum flow of about 15% may constantly be supplied through the heating line/channel.

In some embodiments, the controller may have a modular design to utilize different heating and visualization configurations or use the same temperature control apparatus/system with different sensor hubs located at the imaging system, transportation cart, or preparation room.

In some additional embodiments, the controller may adjust a setting of the cooling fan, the heating fan, and/or the heating block to adjust the temperature of the conditioned air flow. In some aspects, the setting may include the speed of the cooling fan, the speed of the heating fan, or the temperature of the heating block. In some examples, the speed of the cooling fan is adjusted to change the temperature of the conditioned air flow. In still other embodiments, the controller may keep the speed of the heating fan constant to keep the temperature of the heating block stable.

In some embodiments, the controller may be in communication with a server to log data related to the measured temperatures and the adjustments made to the settings of the cooling fan, the heating fan, and/or the heating block.

In some embodiments, the speed of the cooling fan may be adjusted to adjust the temperature of the conditioned air flow. In some aspects, the temperature of the air in the cooling air line may be between about 12° C. to about 22° C. In some embodiments, the air in the cooling air line or in the heating air line may be atmospheric air or it may be purified air. In some examples, the temperature of the air in the cooling air line may be room temperature. In other examples, the temperature of the air in the cooling air line may be below room temperature if a Peltier thermoelectric cooler is attached.

In some embodiments, the speed of the heating fan is adjusted to adjust the temperature of the conditioned air flow. In some aspects, the temperature of the air in the heating air line may be between about 35° C. to about 50° C. In some embodiments, the heating fan may continuously operate to provide a minimum flow rate of hot air to prevent the heating air line from cooling. In some examples, the minimum flow rate of the air in the heating air line may be about 15% of the maximum flow rate of the air in the heating air line.

In some embodiments, the conditioned air flow may have a relative humidity of between about 30% and about 100% or between about 30% and about 50%. The moisture content or relative humidity of the conditioned air flow may be measured with a hygrometer. The hygrometer may be operatively connected to the controller.

In some aspects, the temperature of the conditioned air flow may be between about 32° C. to about 40° C. The temperature of the conditioned air flow may be adjusted related to the target temperature range. The temperature of the conditioned air flow may be adjusted to be higher (i.e., warmer) than the target temperature range to prevent hypothermia caused by anesthesia. The temperature of the conditioned air flow may be adjusted to be lower (i.e., cooler) than the target temperature range to prevent overheating caused by RF heating due to imaging. In an example, the PID controller is a continuous mode controller operable to reduce heating for a temperature above the target and increase heating for a temperature below the target.

In some embodiments, the animal bed system 400 further includes a display 40. In some aspects, the display 40 may be operable to display the temperature of the conditioned air flow, the temperature of the air in the heating air line, and/or the temperature of the air in the cooling air line. In some additional aspects, the display 40 may be operable to display the breathing rate of the animal. In still further aspects, the display 40 may be operable to display the moisture content of the conditioned air flow. In some additional embodiments, the display 40 may be in communication with the controller. The display 40 may be operable to receive inputs from a user. For example, a user may enter information about the animal, a target temperature, or other information about the animal, the temperature, and/or the imaging session.

In some embodiments, the animal bed system 400 may further include a tower 220. In some examples, the display 40 is located on a surface of the tower 220 and the controller and/or sensor hub 30 is located within the tower 220. The temperature control system 10 may be located either outside the tower 220 or inside the tower 220. In some examples, the cooling fan 102, the heating fan 104, and/or the heating block 106 may directly connect to the animal bed apparatus. In other examples, the heating air line and the cooling air line directly connect to the animal bed apparatus.

In some embodiments, the animal bed system may further include an animal ID reader in communication with the controller. The animal ID reader may be operable to read a bar code, a radio frequency identification (RFID) tag, or a quick response (QR) code. The animal ID may include identifying information about the animal. In an example, the animal ID reader is in communication with the controller.

Methods of Maintaining Temperature

Figure 9:
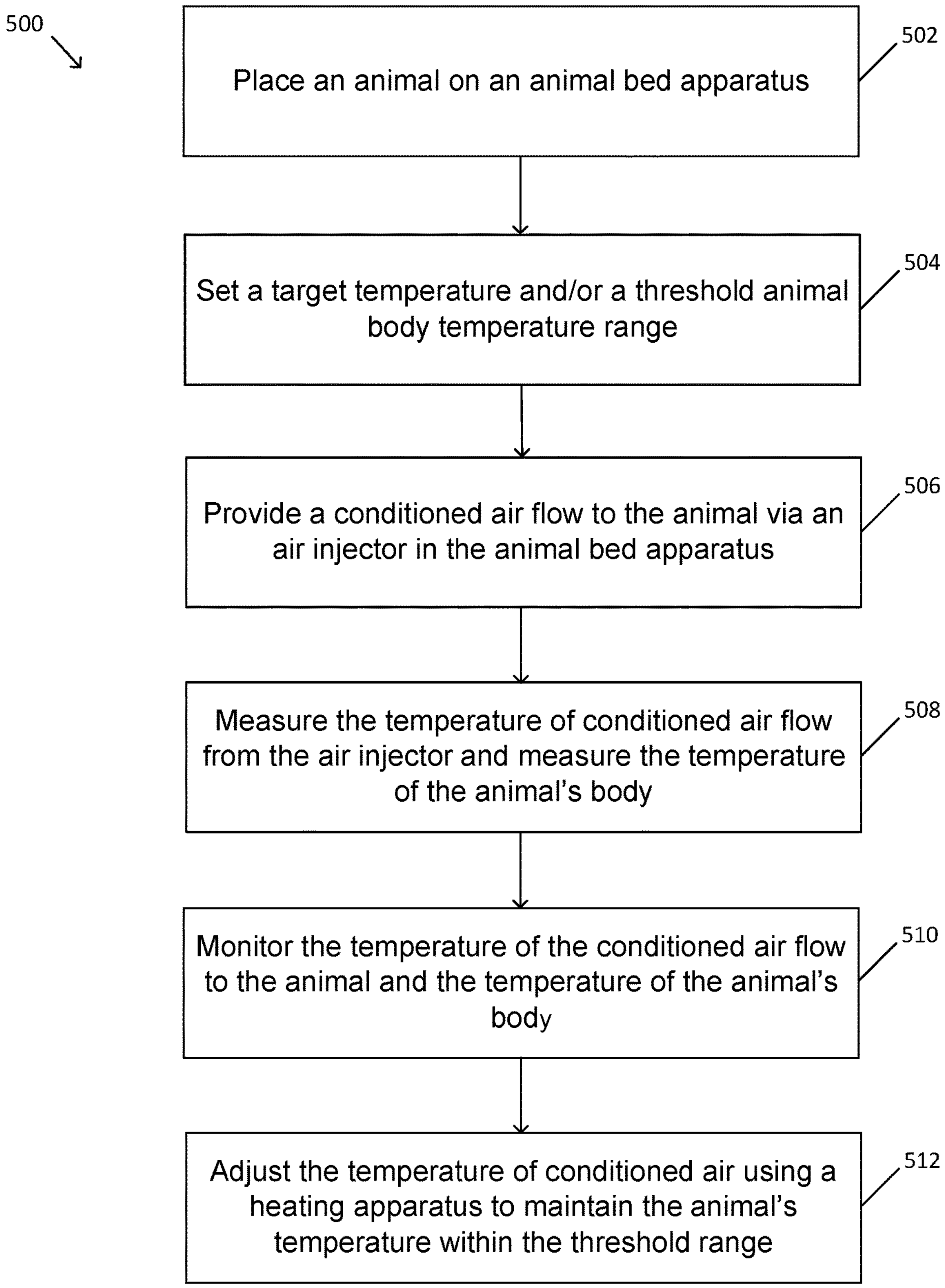
FIG. 9 is a flowchart for methods of maintaining an animal's temperature.

Further provided herein are methods of maintaining an animal's temperature. Referring to FIG. 9, a flowchart is presented in accordance with an example embodiment. The method 500 is provided by way of example, as there are a variety of ways to carry out the method. The method 500 described below can be carried out using the configurations illustrated in FIGS. 1-7, for example, and various elements of these figures are referenced in explaining example method 500. Each block shown in FIG. 9 represents one or more processes, methods or subroutines, carried out in the example method 500. Furthermore, the illustrated order of blocks is illustrative only and the order of the blocks can change according to the present disclosure. Additional blocks may be added or fewer blocks may be utilized, without departing from this disclosure.

The example method 500 is a method of maintaining an animal's temperature while being imaged under anesthesia. The example method 500 can begin at block 502. At block 502, the method includes placing the animal on an animal bed apparatus of the present disclosure. In some embodiments, the animal whose temperature is to be maintained may be a non-human animal. In some aspects, the animal may not be able to regulate its body temperature while under anesthesia for imaging. In some examples, the non-human animal may be a mouse or a rat.

At block 504, the method includes setting a target temperature and/or a target animal body temperature range. Prior to imaging, a target temperature and/or a target temperature range may be determined. The target temperature may be within the target temperature range. The target temperature range may be for a small animal under anesthesia undergoing imaging to prevent hypothermia due to anesthesia and RF heating due to imaging. In some embodiments the target temperature range may be about 36° C.±0.5° C. In other embodiments, the target temperature range may be 32° C. to 40° C. In some embodiments, the target temperature may vary based upon several factors, such as the size of the animal or the species of the animal. In an example, the target temperature is determined for a small animal under anesthesia undergoing imaging to prevent hypothermia due to anesthesia and RF heating due to imaging.

At block 506, the method includes providing a conditioned air flow to the animal vial the air injection in the animal bed apparatus.

At block 608, the method further includes measuring the temperature of the conditioned air flow from the air injector using an air temperature sensor and measuring the temperature of the animal's body using an animal temperature sensor.

At block 510, the method further includes monitoring the temperature of the conditioned air flow to the animal and the temperature of the animal's body using a controller in communication with the temperature control apparatus, air temperature sensor, and the animal temperature sensor.

At block 512, the method further includes adjusting the temperature of the conditioned air directed over the animal using a temperature control apparatus of the present disclosure. In some embodiments, adjusting the temperature of the conditioned air flow corrects the temperature of the animal. The temperature of the conditioned air flow may be automatically adjusted by a controller using a control loop. In some aspects, the control loop may be a P loop, a PI loop, a PID loop, or a double PID loop. In an example, the temperature of the conditioned air flow may be automatically adjusted using a double PID loop. The controller may be in communication with the cooling fan, the heating fan, the heating block, the air temperature sensor, the animal temperature sensor, and optionally additional physiological monitors such as a breathing sensor, heart rate monitors, blood pressure monitors, oxygen saturation monitors, EKG, or pulse monitors.

In some additional embodiments, the step of adjusting the temperature of the conditioned air flow may include adjusting a setting of the cooling fan, the heating fan, and/or the heating block to adjust the temperature of the conditioned air flow. In some aspects, the setting may include the speed of the cooling fan, the speed of the heating fan, or the temperature of the heating block. In some additional aspects, the heating fan speed may be kept constant to keep the heating block temperature stable.

In some embodiments, the method may include adjusting the speed of the cooling fan to adjust the temperature of the conditioned air flow. In some aspects, the temperature of the air in the cooling air line may be between about 12° C. to about 22° C. In some embodiments, the air in the cooling air line or in the heating air line may be atmospheric air or it may be purified air. In some examples, the temperature of the air in the cooling air line may be room temperature.

In some embodiments, the method may include adjusting the speed of the heating fan to adjust the temperature of the conditioned air flow. In some aspects, the temperature of the air in the heating air line may be between about 35° C. to about 50° C. In some embodiments, the heating fan may continuously operate to provide a minimum flow rate of hot air to prevent the heating air line from cooling. In some examples, the minimum flow rate of the air in the heating air line may be about 15% of the maximum flow rate of the air in the heating air line.

In some embodiments, the temperature of the conditioned air flow may be between about 32° C. to about 40° C. The temperature of the conditioned air flow may be adjusted related to the target temperature range. The method may include adjusting the temperature of the conditioned air flow to be higher (i.e., warmer) than the target temperature range to prevent hypothermia caused by anesthesia. The temperature of the conditioned air flow may be adjusted to be lower (i.e., cooler) than the target temperature range to prevent overheating caused by RF heating due to imaging.

In some embodiments, the method may include correcting the temperature of the animal when the temperature of the animal falls outside the target temperature range. In an example, the target temperature range may be about 32° C. to about 40° C., about 35° C. to about 37° C., or about 37° C. to about 39° C. The target temperature may be 35° C.±0.5° C., 36° C.±0.5° C., 37° C.±0.5° C., 38° C.±0.5° C., or 39° C.±0.5° C. In some aspects, the temperature of the animal may be adjusted by adjusting the temperature of the of the conditioned air flow. In an example, the conditioned air temperature is higher (i.e., warmer) than the target temperature range to prevent hypothermia caused by anesthesia. In another example, the conditioned air flow is lower (i.e., cooler) than the target temperature range to prevent overheating caused by RF heating due to imaging. In an example, the PID controller is a continuous mode controller operable to reduce heating for a temperature above the target and increase heating for a temperature below the target.

In an embodiment, the controller automatically maintains the animal's temperature within the target temperature range for a portion of or the duration of the imaging session. In some embodiments, the controller automatically maintains the animal's target temperature within 0.5° C., 1° C., or 2° C. for 1 minute, 2 minutes, 5 minutes, 10 minutes, 30 minutes, or the duration of the imaging session. For example, the temperature control system may maintain an animal target temperature of 35° C.±0.5° C., 36° C.±0.5° C., 37° C.±0.5° C., 38° C.±0.5° C., or 39° C.±0.5° C. for 1 minute, 2 minutes, 5 minutes, 10 minutes, 30 minutes, or the duration of the imaging session.

In some embodiments, the method may further include measuring the moisture content of the conditioned air flow. The conditioned air flow may have a relative humidity of between about 30% and about 100% or between about 30% and 50%. The moisture content or relative humidity of the conditioned air flow may be measured with a hygrometer.

In some embodiments, the method further includes measuring the breathing rate of the animal using a pressure sensor. In some aspects, the pressure sensor may be operable to detect when the animal inhales and exhales. In some examples, the pressure sensor is a differential pressure sensor connected to a respiratory pillow. In some additional aspects, the pressure sensor may be in communication with the controller.

In some embodiments, the method may further include displaying the temperature of the conditioned air flow on a display. The display may be in communication with a controller. In some embodiments, the display may be located on a surface of a tower. In some additional aspects, the controller may be located within the tower. In yet additional aspects, the tower may further comprise a sensor hub with at least two thermocouple ports operable to connect to the air temperature sensor and the animal temperature sensor.

In still additional aspects, the tower may include an animal ID reader. The animal ID reader may be operable to read a bar code, a radio frequency identification (RFID) tag, or a quick response (QR) code. The animal ID may include identifying information about the animal. In an example, the animal ID reader is in communication with the controller.

In some embodiments, the method may reduce the incidence of temperature-related mortality. As used herein, "temperature-related mortality" refers to the mortality rate of animals whose deaths are caused by increased body temperatures (i.e., from RF deposition to the body during imaging) or decreased body temperatures (i.e., from hypothermia caused by anesthesia during imaging). Temperatures above 41° C. are considered dangerous for tissues and organs (protein denature and other effects). The increased or decreased body temperature may be sustained by the animal for an extended period of time before causing death, or the increased or decreased body temperature may be sustained by the animal for a brief period of time before causing death. A reduction in the mortality rate of animals thus refers to a smaller percentage of animals dying as a result of increased or decreased body temperature during imaging compared to a control group.

In some aspects, the method may reduce the incidence of temperature-related mortality by at least 10% up to at least 50%. In some additional aspects, the method may reduce the incidence of temperature-related mortality by at least 10% to at least 15%, at least 15% to at least 20%, at least 20% to at least 25%, at least 25% to at least 30%, at least 30% to at least 35%, at least 35% to at least 40%, at least 40% to at least 45%, or at least 45% to at least 50%. In still other aspects, the method may reduce the incidence of temperature-related mortality by at least 10%, 15%, 20%, 25%, 30%, 35%, 40%, 45%, or at least 50%.

Method of Imaging

Figure 10:
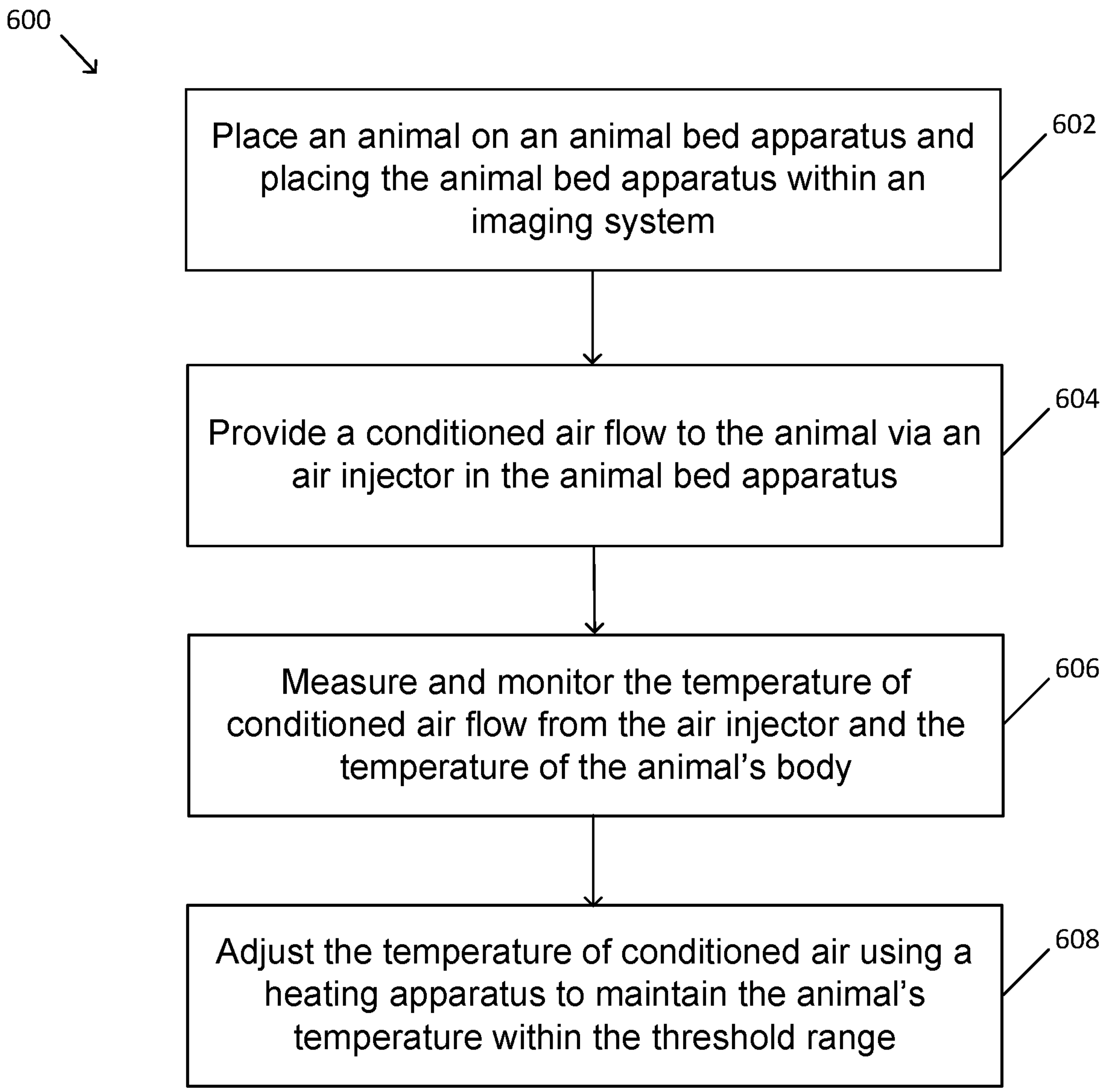
FIG. 10 is a flowchart for methods of imaging an animal in a controlled temperature environment.

Further provided herein are methods of imaging an animal in a controlled temperature environment. Referring to FIG. 10, a flowchart is presented in accordance with an example embodiment. The method 600 is provided by way of example, as there are a variety of ways to carry out the method. The method 600 described below can be carried out using the configurations illustrated in FIGS. 1-7, for example, and various elements of these figures are referenced in explaining example method 600. Each block shown in FIG. 10 represents one or more processes, methods or subroutines, carried out in the example method 600. Furthermore, the illustrated order of blocks is illustrative only and the order of the blocks can change according to the present disclosure. Additional blocks may be added or fewer blocks may be utilized, without departing from this disclosure.

The example method 600 is a method of imaging an animal under anesthesia in a controlled environment. The example method 600 can begin at block 602. At block 602, the method includes placing the animal under anesthesia on an animal bed apparatus and placing the animal bed apparatus with the animal within an imaging system. In some embodiments, the animal may be a non-human animal. In some aspects, the non-human animal may not be able to regulate its body temperature while under anesthesia for imaging. In some examples, the non-human animal may be a mouse or a rat. In some embodiments, the animal bed apparatus may include a base. The base includes a cooling air inlet, a heating air inlet, an injection zone operable to combine air form the cooling air line and the heating air line to create conditioned air, and an air injector operable to direct the conditioned air over the animal.

At block 604, the method includes providing a conditioned air flow to the animal via an air injector in the animal bed apparatus.

At block 606, the method further includes measuring and monitoring the temperature of the conditioned air flow from the air injector using an air temperature sensor and the temperature of the animal using an animal temperature sensor. In some embodiments, the step of measuring the temperature of the conditioned air flow from the air injector using an air temperature sensor does not compromise the imaging. Monitoring the temperature of the conditioned air flow to the animal and the temperature of the animal's body may use a controller in communication with the temperature control apparatus, air temperature sensor, and animal temperature sensor.

At block 608, the method further includes adjusting a temperature of conditioned air directed over the animal using a temperature control apparatus. In some embodiments, the temperature control apparatus includes a cooling fan operatively connected to a cooling air line, a heating fan operatively connected to a heating air line, and a heating block operatively connected to the heating fan and the heating air line. In some aspects, the cooling air line is connected to the cooling air line inlet and the heating air line is connected to the heating air line inlet.

In some embodiments, the method further includes measuring the breathing rate of the animal using a pressure sensor. In some aspects, the pressure sensor may be operable to detect when the animal inhales and exhales. In some examples, the pressure sensor is a differential pressure sensor connected to a respiratory pillow.

In some embodiments, the method may further include adjusting the temperature of the conditioned air flow to correct the temperature of the animal. The temperature of the conditioned air flow may be adjusted by a controller. In some aspects, the controller may adjust the temperature of the conditioned air flow automatically using a P loop, a PI loop, a PID loop, or a double PID loop. In an example, the controller adjusts the temperature of the conditioned air flow automatically using a double PID loop. The controller may be in communication with the cooling fan, the heating fan, the heating block, the air temperature sensor, the animal temperature sensor, and optionally additional physiological monitors such as a breathing sensor, heart rate monitors, blood pressure monitors, oxygen saturation monitors, EKG, or pulse monitors.

In some aspects, adjusting the temperature of the conditioned air flow includes adjusting a setting of the cooling fan, the heating fan, and/or the heating block. The setting may include the speed of the cooling fan, the speed of the heating fan, or the temperature of the heating block. In some examples, the speed of the heating fan is constant to keep the heating block temperature stable. In some additional examples, the speed of the cooling fan is adjusted to change the temperature of the conditioned air flow.

Prior to imaging, a target temperature and/or a target temperature range may be determined. The target temperature may be within the target temperature range. The target temperature range may be for a small animal under anesthesia undergoing imaging to prevent hypothermia due to anesthesia and RF heating due to imaging. In some embodiments the target temperature range may be about 36° C.±0.5° C., about 32° C. to 40° C., about 35° C. to 37° C., about 35° C. to 38° C., or about 37° C. to about 39° C. The target temperature may be 35° C.±0.5° C., 36° C.±0.5° C., 37° C.±0.5° C., 38° C.±0.5° C., or 39° C.±0.5° C. In some embodiments, the target temperature may vary based upon several factors, such as the size of the animal or the species of the animal. In an example, the target temperature is determined for a small animal under anesthesia undergoing imaging to prevent hypothermia due to anesthesia and RF heating due to imaging.

In some embodiments, the PID controller automatically adjusts the speed of the flow rate of the cooling fan and/or the heating fan to reduce heating for a temperature above the target and increase heating for a temperature below the target. In an embodiment, the controller automatically maintains the animal's temperature within the target temperature range for a portion of or the duration of the imaging session. In some embodiments, the controller automatically maintains the animal's target temperature within 0.5° C., 1° C., or 2° C. for 1 minute, 2 minutes, 5 minutes, 10 minutes, 30 minutes, or the duration of the imaging session. For example, the temperature control system maintains an animal target temperature of 35° C.±0.5° C., 36° C.±0.5° C., 37° C.±0.5° C., 38° C.±0.5° C., or 39° C.±0.5° C. for 1 minute, 2 minutes, 5 minutes, 10 minutes, 30 minutes, or the duration of the imaging session.

In some embodiments, the method may include adjusting the speed of the cooling fan to adjust the temperature of the conditioned air flow. In some aspects, the temperature of the air in the cooling air line may be between about 12° C. to about 22° C. In some embodiments, the air in the cooling air line or in the heating air line may be atmospheric air or it may be purified air. In some examples, the temperature of the air in the cooling air line may be room temperature.

In some embodiments, the method may include adjusting the speed of the heating fan to adjust the temperature of the conditioned air flow. In some aspects, the temperature of the air in the heating air line may be between about 35° C. to about 50° C. In some embodiments, the heating fan may continuously operate to provide a minimum flow rate of hot air to prevent the heating air line from cooling. In some examples, the minimum flow rate of the air in the heating air line may be about 15% of the maximum flow rate of the air in the heating air line.

In some embodiments, the method may include measuring the moisture content of the conditioned air flow. The conditioned air flow may have a relative humidity of between about 30% and about 100% or between about 30% and 50%. The moisture content or relative humidity of the conditioned air flow may be measured with a hygrometer.

In some embodiments, the temperature of the conditioned air flow may be between about 32° C. to about 40° C. The temperature of the conditioned air flow may be adjusted related to the target temperature range. The method may include adjusting the temperature of the conditioned air flow to be higher (i.e., warmer) than the target temperature range to prevent hypothermia caused by anesthesia. The temperature of the conditioned air flow may be adjusted to be lower (i.e., cooler) than the target temperature range to prevent overheating caused by RF heating due to imaging.

In some embodiments, the method may include correcting the temperature of the animal when the temperature of the animal falls outside the target temperature range. In some aspects, the temperature of the animal may be adjusted by adjusting the temperature of the of the conditioned air flow. In an example, the conditioned air temperature is higher (i.e., warmer) than the target temperature range to prevent hypothermia caused by anesthesia. In another example, the conditioned air flow is lower (i.e., cooler) than the target temperature range to prevent overheating caused by RF heating due to imaging. In an example, the PID controller is a continuous mode controller operable to reduce heating for a temperature above the target and increase heating for a temperature below the target.

In some embodiments, the method may include displaying the temperature of the conditioned airflow on a display. In some aspects, the display may be located on a surface of a tower. In embodiments that include a controller, the controller may be located within the tower. In some additional aspects, the sensor hub may further include at least two thermocouple ports operable to connect to the air temperature sensor and the animal temperature sensor. The sensor hub may be located within the tower. In still further aspects, the tower may further comprise an animal ID reader. In embodiments that include a controller, the animal ID reader may be in communication with the controller. The animal ID reader may be operable to read a bar code, a radio frequency identification (RFID) tag, or a quick response (QR) code. The animal ID may include identifying information about the animal.

In some embodiments, the method may reduce the incidence of temperature-related mortality by at least 10% up to at least 50%. In some additional aspects, the method may reduce the incidence of temperature-related mortality by at least 10% to at least 15%, at least 15% to at least 20%, at least 20% to at least 25%, at least 25% to at least 30%, at least 30% to at least 35%, at least 35% to at least 40%, at least 40% to at least 45%, or at least 45% to at least 50%. In still other aspects, the method may reduce the incidence of temperature-related mortality by at least 10%, 15%, 20%, 25%, 30%, 35%, 40%, 45%, or at least 50%.

EXAMPLES

Example 1

Figure 11:
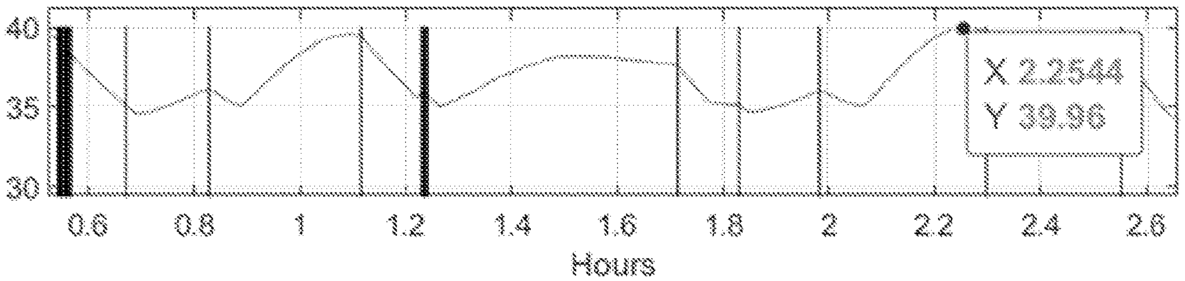
FIG. 11 shows the animal body temperature during an experiment with a single channel PID controller.

A single loop PID controller was tested for maintaining animal temperature similar to those available commercially show that it is unsafe for animals during oxygen imaging experiments as shown in FIG. 11. FIG. 11 shows the animal body temperature during an experiment with a single channel PID controller that controls the temperature of the air heating element (air flow is constant). At the time when the measurement and heat deposition is started a rise of the temperature is observed. The controller reduced the heat, but thermal inertia prevented immediate cooling of the air in the heater and supply lines and an overshoot of the animal temperature was observed. When the measurement was finished, cooled down heater and supply lines take time to warm up leaving animal cold for substantial time. Therefore, current solutions for maintaining animal well-being are inadequate for EPROI experiments. Similar problems exist in MRI experiments.

Example 2

Figure 12:
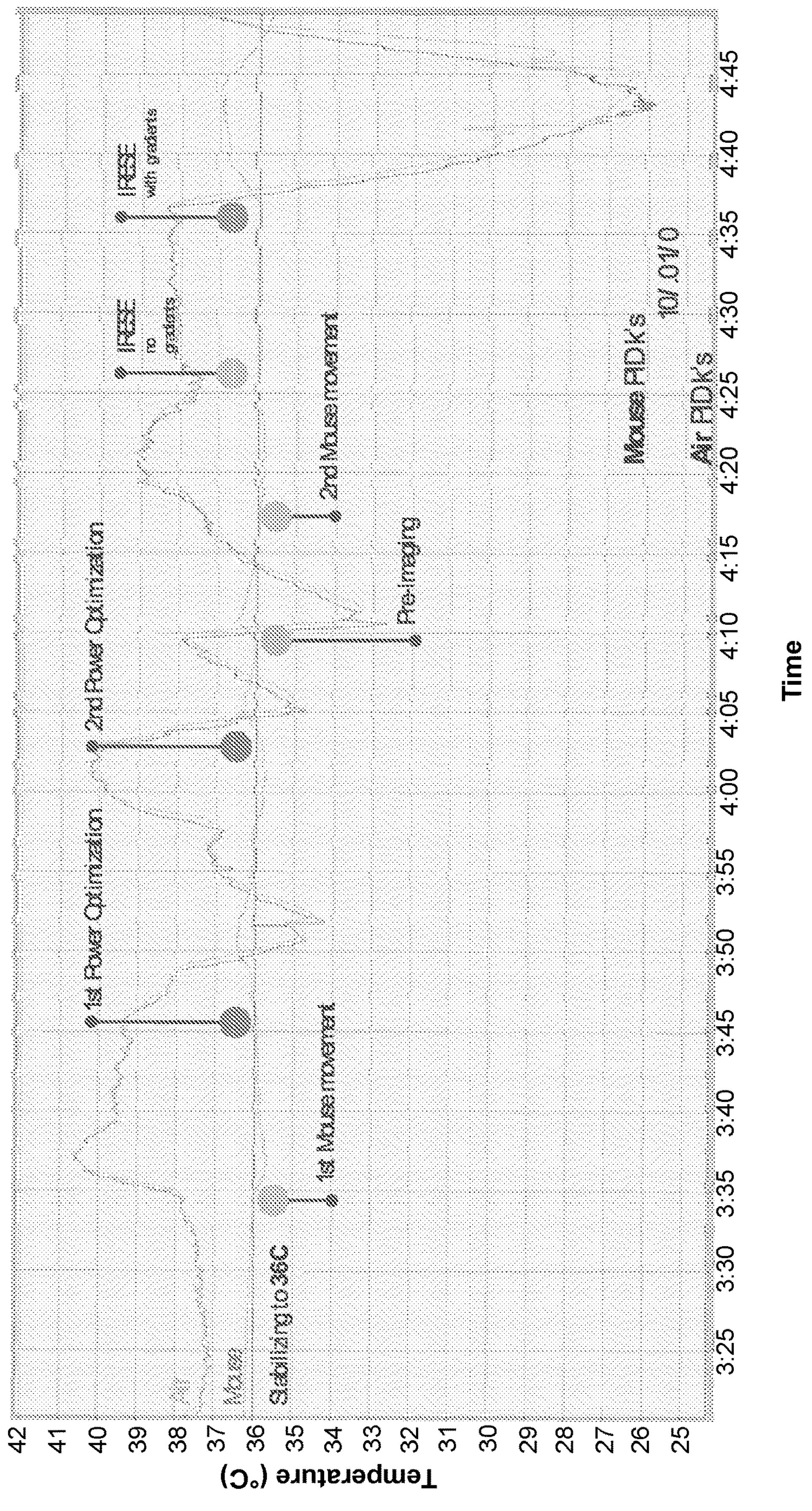
FIG. 12 shows the temperature trace (red) of an animal during the resting and oxygen imaging sequence along with the air temperature trace (blue/black) while using the temperature control system with a double PID loop.

The system disclosed herein using a double PID loop was used to maintain the temperature of a mouse being imaged using EPROI. FIG. 12 shows the temperature trace (red) of an animal during the resting and oxygen imaging sequence along with the air temperature trace (blue/black). It is interesting to see that during the non-imaging resting period, the mouse is cold due to anesthesia and therefore it needs to be heated. The heat is provided by warm air that is few degrees higher than the target temperature of 37° C. Once the imaging sequence starts, the RF pulses deposit energy to the animal and it starts heating, therefore cooling kicks in and it can be seen that the animal temperature is maintained within 0.5° C. of the target temperature while the air temperature is colder than the animal target temperature. The experiments with more animals showed similar results confirming the resilience of the smart temperature control system.

Example 3

Figure 13:
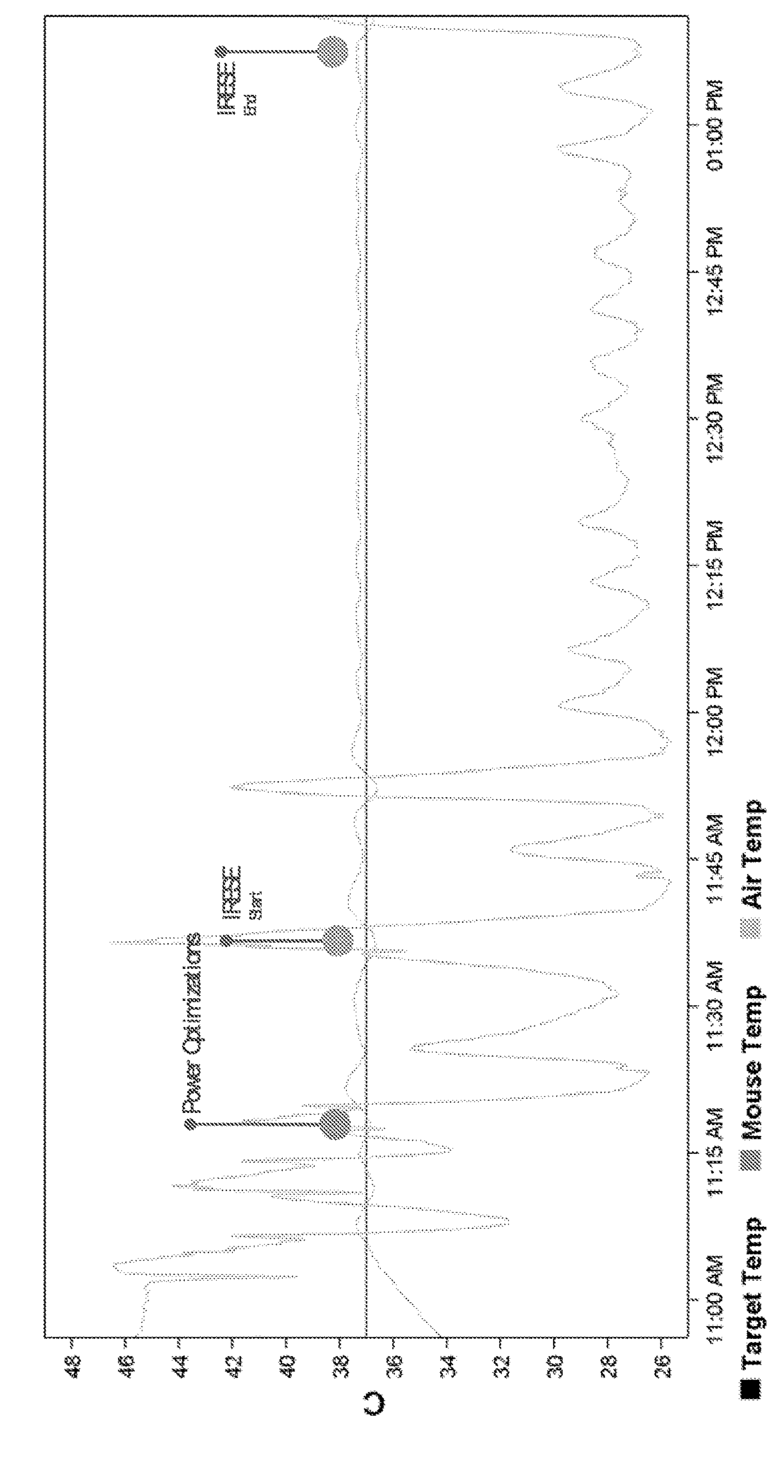
FIG. 13 shows the temperature trace (red) of an animal during a 2 hour and 15 minute imaging sequence along with the air temperature trance (blue).

FIG. 13 shows the temperature trace (red) of an animal during a 2 hour and 15 minute imaging sequence along with the air temperature trance (blue). As can be seen, when the imaging begins, the mouse temperature increases and the air temperature begins to decrease. After about an hour, the air temperature was consistently below the target temperature of 37° C. as the mouse absorbed RF heat from the imaging process.

Example 4

Figure 14:
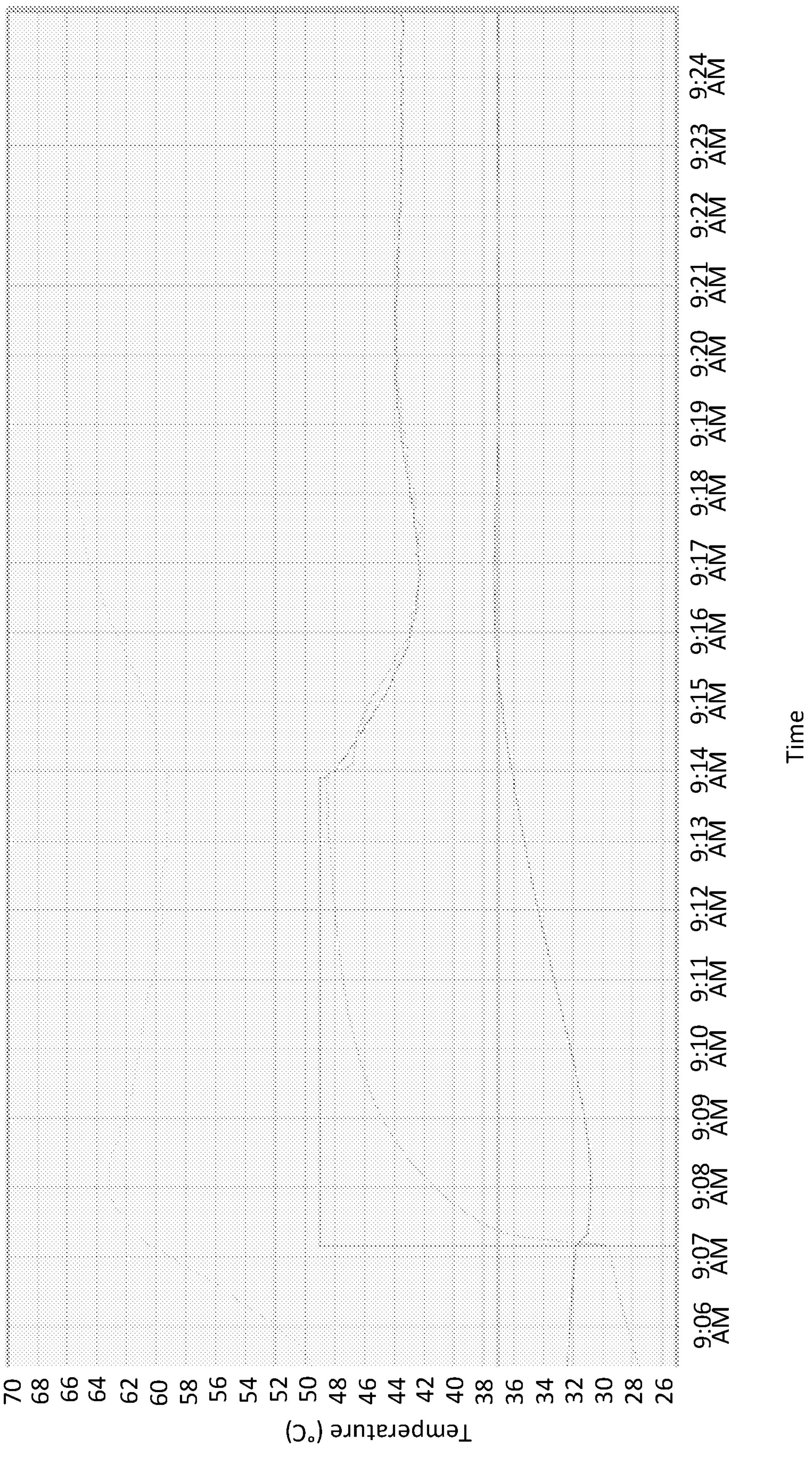
FIG. 14 shows the temperature trace (red) of an animal model during a warmup test along with the air temperature trace (blue) and the heater temperature trace (yellow) during a warmup step test.

FIG. 14 shows the temperature trace (red) of an animal model during a warmup test along with the air temperature trace (blue) and the heater temperature trace (yellow) during a warmup step test. The inner PID only ran the cold fan. The range of the cold fan was extended by driving the controller backwards. The hot fan speed was kept constant to keep the heater temperature stable. The PID loop started at about 9:07 AM on the graph at 60° C., where the air temperature target was adjusted to about 49° C. The integrals defaulted when the animal model temperature reached 36° C. The animal model's temperature reached a maximum of 37.3° C.

Example 5

Figure 15:
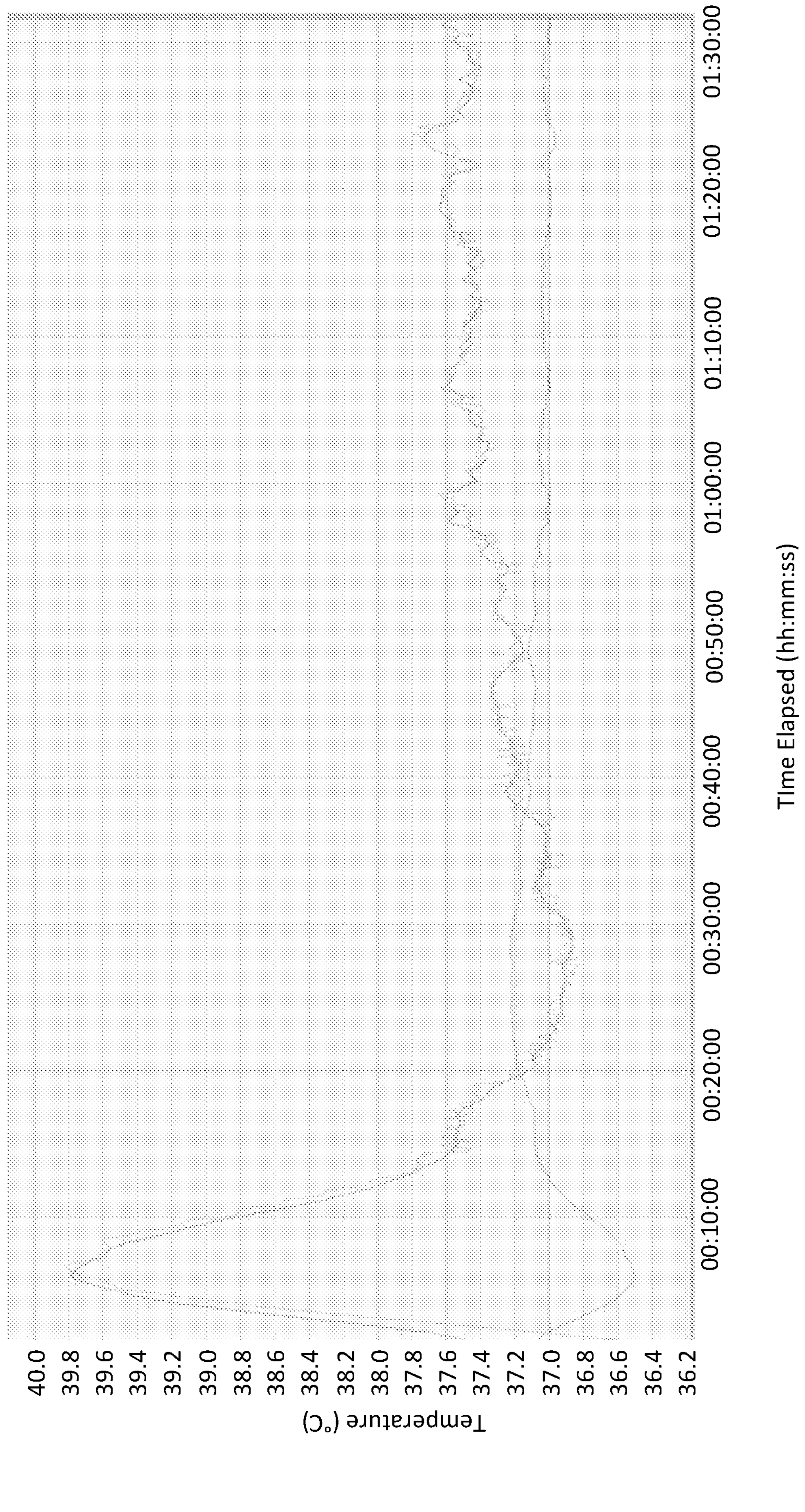
FIG. 15 shows the temperature trace (red) of a mouse along with the air temperature trace (blue) and the target air temperature (grey) during an imaging test.

FIG. 15 shows the temperature trace (red) of a mouse along with the air temperature trace (blue) and the target air temperature (grey) during an imaging test. The target temperature was 37.0° C. The mouse was a C57 mouse weighing 13 g. As can be seen from the figure, the mouse temperature began to drop at the beginning of the test and the air temperature increased in response until the mouse's body temperature rose above the target temperature. Once the mouse temperature rose above the target temperature, the air temperature began to cool. As the mouse temperature gradually decreased, the air temperature gradually increased to prevent the mouse temperature from falling below the target temperature.

Example 6

Figure 16:
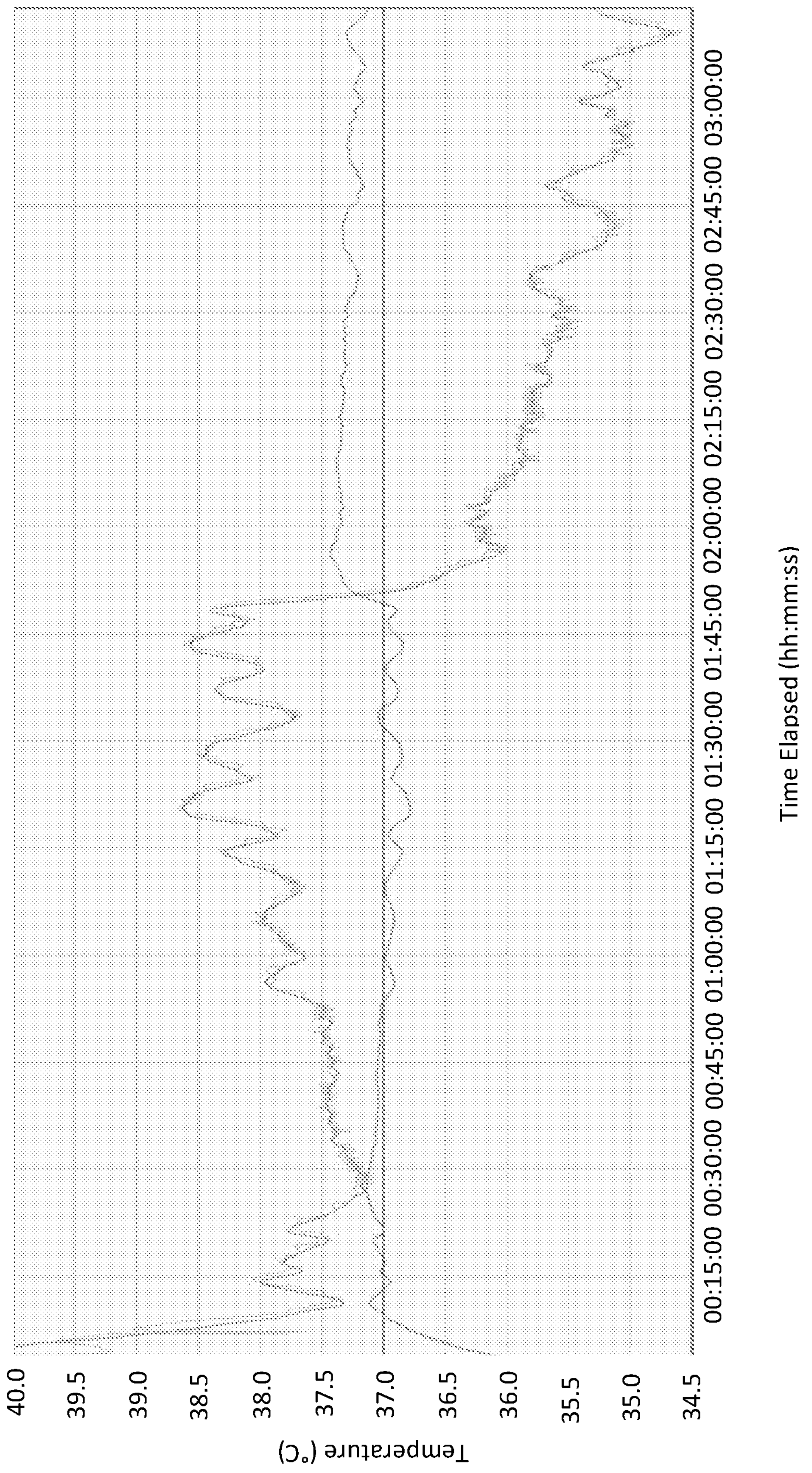
FIG. 16 shows the temperature trace (red) of a mouse along with the air temperature trace (blue) and the target air temperature (grey) during an imaging test.

FIG. 16 shows the temperature trace (red) of a mouse along with the air temperature trace (blue) and the target air temperature (grey) during an imaging test. The mouse target temperature was 37.0° C. The mouse was a C57 mouse weighing 15.5 g. Imaging began shortly after the 1:45:00 time mark. As can be seen from the figure, the mouse temperature sharply increased when imaging began, and the air temperature sharply decreased in response. This prevented the mouse's body temperature from rising above 37.5° C.

Example 7

Figure 17:
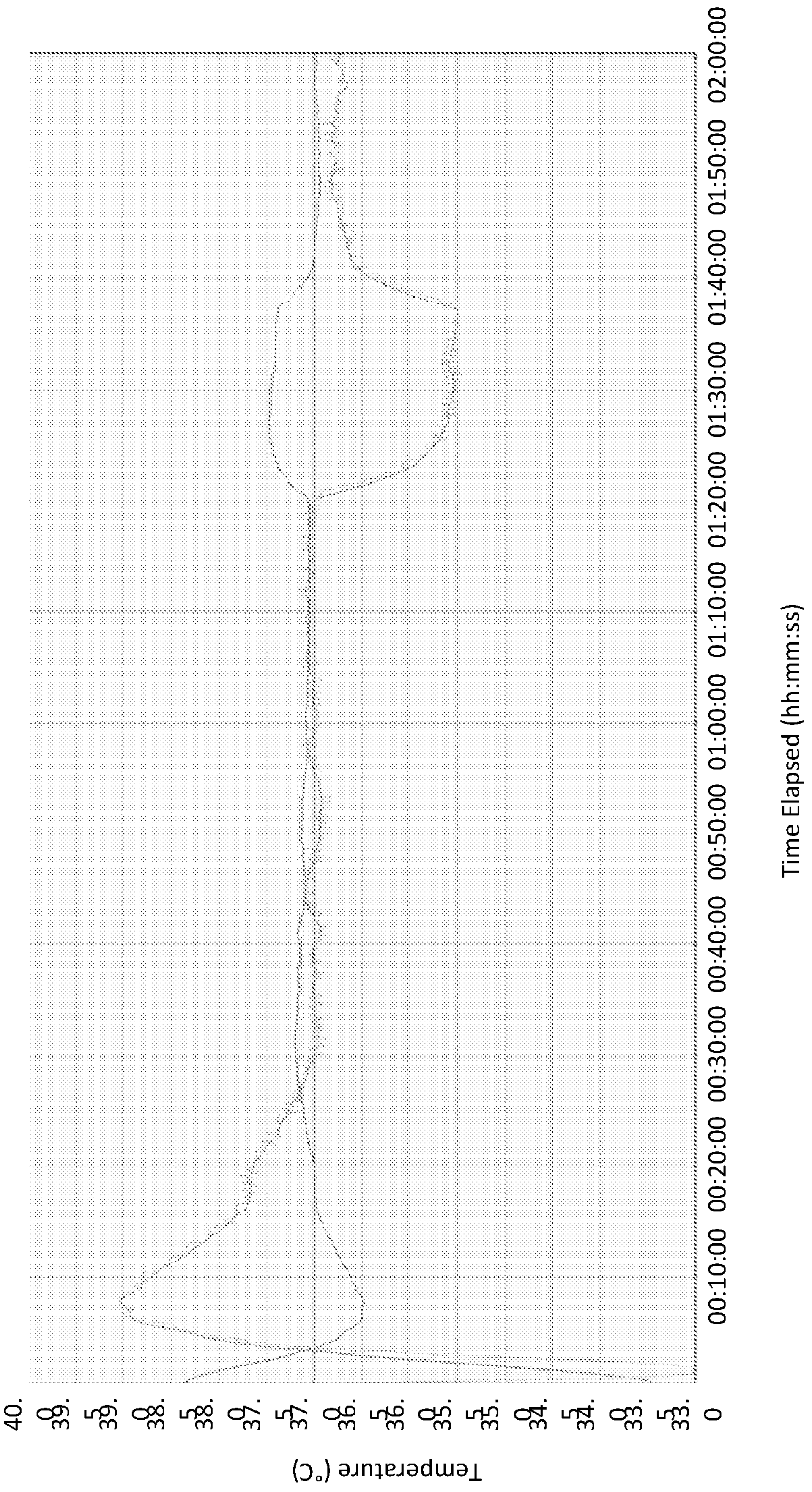
FIG. 17 shows the temperature trace (red) of a mouse along with the air temperature trace (blue) and the air target temperature (grey) during an imaging test.

FIG. 17 shows the temperature trace (red) of a mouse along with the air temperature trace (blue) and the air target temperature (grey) during an imaging test. The mouse target temperature was 37.0° C. The mouse was a C57 mouse weighing 13.5 g. Imaging began shortly after the 1:20:00 mark and ended shortly before the 1:40:00 mark. As can be seen from the figure, prior to imaging, the mouse's body temperature decreased and the air temperature increased in response. The air temperature and mouse temperature then stabilized at a temperature close to 37° C. Once imaging began, the mouse's body temperature sharply increased and the air temperature sharply decreased in response, preventing the mouse's body temperature from rising above 37.5° C. When imaging ended, the mouse's body temperature began decreasing, and the air temperature increased in response.

Example 8

Figure 18:
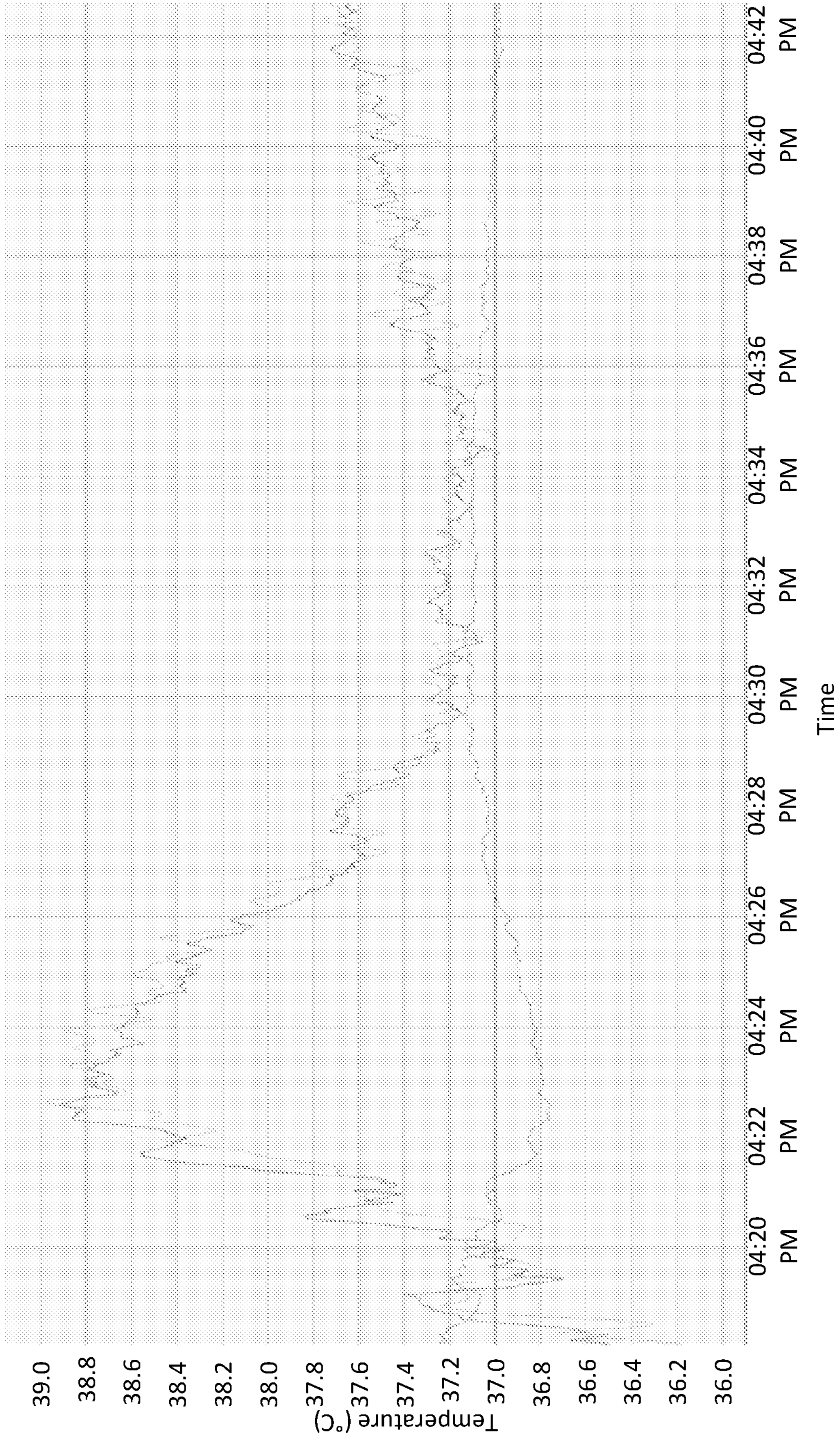
FIG. 18 shows the temperature trace (red) of a mouse along with the air temperature trace (blue) and the air target temperature (grey) during an imaging test.

FIG. 18 shows the temperature trace (red) of a mouse along with the air temperature trace (blue) and the air target temperature (grey) during an imaging test. The mouse target temperature was 37.0° C. As can be seen from the figure, the air temperature rapidly adjusts in response to the changing mouse temperature.

Example 9

Figure 19:
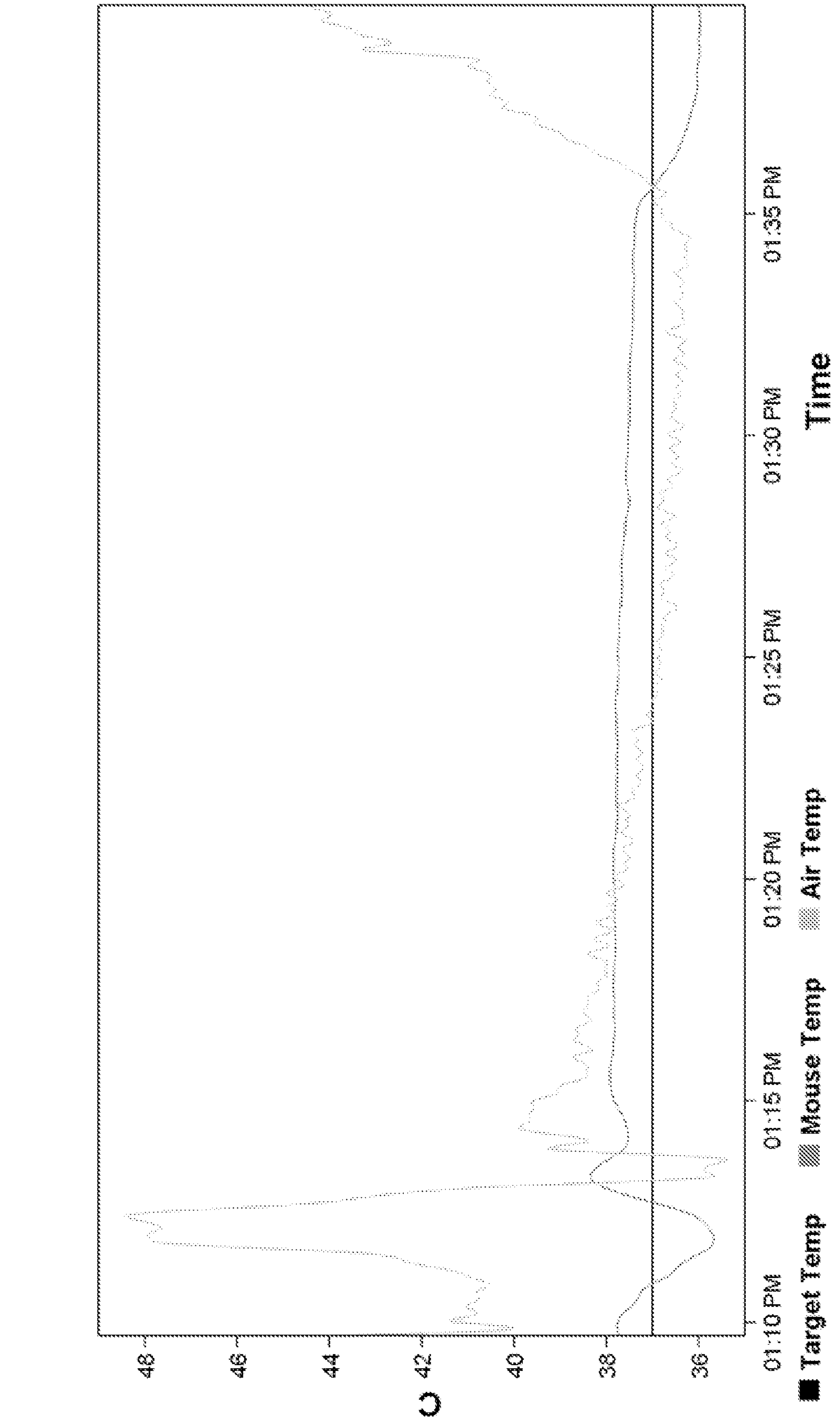
FIG. 19 shows the temperature trace (red) of a mouse along with the air temperature trace (blue) and the air target temperature (grey).

FIG. 19 shows the temperature trace (red) of a mouse along with the air temperature trace (blue) and the air target temperature (grey). The mouse target temperature was 37.0° C. Imaging began shortly after the 1:15 PM mark after the first power optimization. Imaging ended shortly after the 1:35 PM mark. As can be seen, the mouse's temperature quickly rose at the beginning of the test when the air temperature increased. After imaging began, the mouse's temperature remained consistently higher than the target temperature as the air temperature gradually decreased. Once imaging ended, the mouse's temperature quickly decreased, and the air temperature quickly increased in response.

Example 10

Figure 20:
FIG. 20 shows the temperature trace (red) of an animal model along with the air temperature trace (blue) and the air target temperature trace (blue) in a step test conducted with an animal model.

FIG. 20 shows the temperature trace (red) of an animal model along with the air temperature trace (blue) and the air target temperature trace (blue) in a step test conducted with an animal model. The Figure shows the response of the heater system when the temperature of the animal model is increased or decreased by 1° C. steps. The maximum overshoot was 0.3° C. and the maximum undershoot was 0.1° C.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

EXEMPLARY EMBODIMENTS

Embodiment 1: A temperature control apparatus for heating or cooling an animal under anesthesia for imaging, the apparatus comprising: a cooling fan operatively connected to a cooling air line; a heating fan operatively connected to a heating air line; a heating block operatively connected to the heating fan and the heating air line to heat the air within the heating air line; and a housing, wherein the cooling fan, heating fan, and heating block are located within the housing.

Embodiment 2: The temperature control apparatus of embodiment 1, wherein the housing further comprises an air inlet operatively connected to the cooling fan to introduce room temperature air into the cooling air line.

Embodiment 3: The temperature control apparatus of embodiment 1, wherein the housing further comprises a cooling air line outlet and a heating air line outlet.

Embodiment 4: The temperature control apparatus of embodiment 3, wherein the cooling air line outlet comprises an indicator that air is flowing through the cooling air line and the heating air line outlet comprises an indicator that air is flowing through the heating air line.

Embodiment 5: The temperature control apparatus of embodiment 4, wherein the indicator on the cooling air line outlet and the indicator on the heating air line outlet is a light surrounding or projecting from the respective outlet.

Embodiment 6: The temperature control apparatus of embodiment 1, wherein the animal is a non-human animal.

Embodiment 7: The temperature control apparatus of embodiment 6, wherein the non-human animal is a mouse or a rat.

Embodiment 8: The temperature control apparatus of embodiment 1, wherein the animal is not able to regulate body temperature while under anesthesia for imaging.

Embodiment 9: The temperature control apparatus of embodiment 1, further comprising a Peltier cooler connected to the cooling fan.

Embodiment 10: The temperature control apparatus of embodiment 1, wherein the temperature of the air in the cooling air line ranges from 12° C. to 22° C.

Embodiment 11: The temperature control apparatus of embodiment 1, wherein the temperature of the air in the heating air line ranges from 35° C. to 50° C.

Embodiment 12: The temperature control apparatus of embodiment 1, wherein the temperature of a combination of the air in the cooling air line and the heating air line ranges from 32° C. to 40° C.

Embodiment 13: The temperature control apparatus of embodiment 12, wherein the temperature of the combination of the air in the cooling air line and the heating air line may be changed within 10 seconds after adjusting the cooling fan, the heating fan, and/or the heating block.

Embodiment 14: The temperature control apparatus of embodiment 13, wherein the change in the temperature of the combination of air changes the temperature of the animal within 1 minute.

Embodiment 15: The temperature control apparatus of embodiment 12, further comprising a display operable to display the temperature of the air in the cooling air line, the temperature of the air in the heating air line, and/or the temperature of the combination of the air in the cooling air line and the heating air line.

Embodiment 16: The temperature control apparatus of embodiment 1, wherein the imaging is magnetic resonance imaging (MRI), positron emission tomography (PET), computed tomography (CT), and pulse electron paramagnetic resonance oxygen imaging (EPROI).

Embodiment 17: A system for heating or cooling an animal under anesthesia for imaging, the system comprising: a temperature control apparatus comprising: a cooling fan operatively connected to a cooling air line; a heating fan operatively connected to a heating air line; a heating block operatively connected to the heating fan and the heating air line to heat the air within the heating air line; and a housing, wherein the cooling fan, the heating fan, and the heating block are located within the housing; an air temperature sensor operable to measure the temperature of a conditioned air flow from the cooling air line and the heating air line; an animal temperature sensor operable to measure the temperature of the animal's body; and a controller in communication with the temperature control apparatus, the air temperature sensor, and the animal temperature sensor, and operable to monitor the temperature of the conditioned air flow to the animal and the temperature of the animal's body.

Embodiment 18: The system of embodiment 17, further comprising a pressure sensor operable to measure the breathing rate of the animal.

Embodiment 19: The system of embodiment 17, wherein the controller is operable to adjust the temperature of the conditioned air flow to correct the temperature of the animal.

Embodiment 20: The system of embodiment 19, wherein the controller is a proportional-integral-derivative (PID) controller operable to automatically adjust the temperature of the conditioned air flow.

Embodiment 21: The system of embodiment 19, wherein the controller adjusts a setting of the cooling fan and/or the heating fan to adjust the temperature of the conditioned air flow.

Embodiment 22: The system of embodiment 19, wherein the heating fan speed is constant to keep the heating block temperature stable.

Embodiment 23: The system of embodiment 19, wherein the speed of the of the cooling fan is adjusted to change the temperature of the conditioned air flow.

Embodiment 24: The system of embodiment 19, wherein the temperature of the air in the cooling air line ranges from 12° C. to 22° C.

Embodiment 25: The system of embodiment 19, wherein the temperature of the air in the heating air line ranges from 35° C. to 50° C.

Embodiment 26: The system of embodiment 19, wherein the temperature of the conditioned air flow ranges from 32° C. to 40° C.

Embodiment 27: The system of embodiment 26, wherein the conditioned air has a relative humidity ranging from 30% to 50%.

Embodiment 28: The system of embodiment 19, wherein the temperature of the animal needs to be corrected when it falls outside a target temperature range.

Embodiment 29: The system of embodiment 28, wherein the target temperature range is determined for a small animal under anesthesia undergoing imaging to prevent hypothermia due to anesthesia and RF heating due to imaging.

Embodiment 30: The system of embodiment 28, wherein the target temperature range is 32° C. to 40° C.

Embodiment 31: The system of embodiment 28, wherein the conditioned air temperature is warmer than the target temperature range to adjust for the anesthesia and the conditioned air temperature is lower than the target temperature range to adjust for RF heating due to the imaging.

Embodiment 32: The system of embodiment 17, further comprising a display operable to display the temperature of the conditioned air flow.

Embodiment 33: The system of embodiment 32, further comprising a tower, wherein the display is located on a surface of the tower and the controller is located within the tower.

Embodiment 34: The system of embodiment 17, wherein the controller is further in communication with a server to log data related to the measured temperatures.

Embodiment 35: The system of embodiment 17, further comprising a sensor hub with at least two thermocouple ports operable to connect to the air temperature sensor and the animal temperature sensor.

Embodiment 36: The system of embodiment 17, further comprising an animal ID reader in communication with the controller.

Embodiment 37: The system of embodiment 17, wherein the animal is a mouse or a rat.

Embodiment 38: An animal bed apparatus for imaging comprising: an animal bed comprising: a support surface having a first longitudinal side and a second longitudinal side, wherein the support surface is operable to hold an animal; and a pair of rails along at least a portion of the first longitudinal side and the second longitudinal side; a mask connected to the animal bed and operable to hold anesthesia over the animal; an anesthesia inlet operably connected to the mask and operable to be connected to an anesthesia source via an anesthesia line; a base comprising rail slots along a first longitudinal edge and a second longitudinal edge, wherein the rail on the portion of the first longitudinal side of the animal bed surface is operable to slide within the rail slot along the first longitudinal edge of the base and the rail on the portion of the second longitudinal side of the animal bed surface is operable to slide within the rail slot along the second longitudinal edge of the base; and an air injector connected to the base and operable to blow conditioned air over the animal on the animal bed.

Embodiment 39: The animal bed apparatus of embodiment 38, wherein the air injector is circular in shape with an opening such that the animal bed can slide through the opening of the air injector.

Embodiment 40: The animal bed apparatus of embodiment 38, wherein the base further comprises a cooling air line inlet operable to connect to a cooling air line from a temperature control apparatus and a heating air line inlet operable to connect to a heating air line from the temperature control apparatus.

Embodiment 41: The animal bed apparatus of embodiment 40, wherein the base further comprises an injection zone operable to combine air from the cooling air line and the heating air line, creating the conditioned air that is blown over the animal at the air injector.

Embodiment 42: The animal bed apparatus of embodiment 38, further comprising: a temperature sensor operable to measure a temperature of the animal; and a breathing sensor operable to measure a breathing rate of the animal.

Embodiment 43: The animal bed apparatus of embodiment 42, further comprising a controller operable to: communicate the temperature of the animal to a temperature control apparatus; and control delivery of anesthesia to the animal.

Embodiment 44: The animal bed apparatus of embodiment 43, further comprising a display operable to display the temperature of the animal and the breathing rate of the animal.

Embodiment 45: The animal bed apparatus of embodiment 44, further comprising a tower connected to the base for properly positioning the animal bed and the base within an imaging system.

Embodiment 46: The animal bed apparatus of embodiment 45, wherein the display is located on the tower and the controller is located within the support.

Embodiment 47: The animal bed apparatus of embodiment 46, wherein the tower further comprises an anesthesia splitter comprising a supply line inlet, an anesthesia outlet, and an exhaust outlet, wherein the supply line inlet is connected to the anesthesia source via a supply line, and wherein the anesthesia outlet is connected to the anesthesia inlet on the animal bed via an anesthesia line.

Embodiment 48: The animal bed apparatus of embodiment 38, wherein the animal is a non-human animal.

Embodiment 49: The animal bed apparatus of embodiment 48, wherein the animal is a mouse or a rat.

Embodiment 50: The animal bed apparatus of embodiment 49, wherein the animal bed is sized to facilitate imaging a limb of the mouse or the rat.

Embodiment 51: The animal bed apparatus of embodiment 49, wherein the animal bed is sized to facilitate imaging of the whole body of the mouse or the rat.

Embodiment 52: An animal bed system for maintaining an animal's temperature while being imaged under anesthesia, the system comprising: a temperature control apparatus comprising: a cooling fan operatively connected to a cooling air line; a heating fan operatively connected to a heating air line; and a heating block operatively connected to the heating fan and the heating air line to heat the air within the heating air line; an animal bed apparatus operable to hold an animal, the animal bed apparatus having a base comprising: a cooling air line inlet, a heating air line inlet, an injection zone operable to combine air from the cooling air line and the heating air line, creating conditioned air, and an air injector operable to direct the conditioned air over the animal, wherein the cooling air line is connected to the cooling air line inlet and the heating air line is connected to the heating air line inlet; an air temperature sensor operable to measure the temperature of the conditioned air from the air injector; an animal temperature sensor operable to measure the temperature of the animal's body; and a controller in communication with the temperature control apparatus, the air temperature sensor, and the animal temperature sensor, and operable to monitor the temperature of the conditioned air to the animal and the temperature of the animal's body.

Embodiment 53: The system of embodiment 52, further comprising a pressure sensor operable to measure the breathing rate of the animal.

Embodiment 54: The system of embodiment 52, wherein the controller is operable to adjust the temperature of the conditioned air flow to correct the temperature of the animal.

Embodiment 55: The system of embodiment 54, wherein the controller is a proportional-integral-derivative (PID) controller operable to automatically adjust the temperature of the conditioned air flow.

Embodiment 56: The system of embodiment 54, wherein the controller adjusts a setting of the cooling fan and/or the heating fan to adjust the temperature of the conditioned air flow.

Embodiment 57: The system of embodiment 54, wherein the heating fan speed is constant to keep the heating block temperature stable.

Embodiment 58: The system of embodiment 54, wherein the speed of the of the cooling fan is adjusted to change the temperature of the conditioned air flow.

Embodiment 59: The system of embodiment 54, wherein the temperature of the air in the cooling air line ranges from 12° C. to 22° C.

Embodiment 60: The system of embodiment 54, wherein the temperature of the air in the heating air line ranges from 35° C. to 50° C.

Embodiment 61: The system of embodiment 54, wherein the temperature of the conditioned air flow ranges from 32° C. to 40° C.

Embodiment 62: The system of embodiment 61, wherein the conditioned air has a relative humidity ranging from 30% to 50%.

Embodiment 63: The system of embodiment 54, wherein the temperature of the animal needs to be corrected when it falls outside a target temperature range.

Embodiment 64: The system of embodiment 63, wherein the target temperature range is determined for a small animal under anesthesia undergoing imaging to prevent hypothermia due to anesthesia and RF heating due to imaging.

Embodiment 65: The system of embodiment 63, wherein the target temperature range is 32° C. to 40° C.

Embodiment 66: The system of embodiment 63, wherein the conditioned air temperature is warmer than the target temperature range to adjust for the anesthesia and the conditioned air temperature is lower than the target temperature range to adjust for RF heating due to the imaging.

Embodiment 67: The system of embodiment 52, further comprising a display operable to display the temperature of the conditioned air flow.

Embodiment 68: The system of embodiment 67, further comprising a tower, wherein the display is located on a surface of the tower and the controller is located within the tower.

Embodiment 69: The system of embodiment 52, wherein the controller is further in communication with a server to log data related to the measured temperatures.

Embodiment 70: The system of embodiment 52, further comprising a sensor hub comprising at least two thermocouple ports operable to connect to the air temperature sensor and the animal temperature sensor.

Embodiment 71: The system of embodiment 52, further comprising an animal ID reader in communication with the controller.

Embodiment 72: The system of embodiment 52, wherein the animal is a mouse or a rat.

Embodiment 73: A method for maintaining an animal's temperature while being imaged under anesthesia, the method comprising: placing the animal on an animal bed apparatus, the animal bed apparatus having a base comprising: a cooling air line inlet, a heating air line inlet, an injection zone operable to combine air from the cooling air line and the heating air line, creating conditioned air, and an air injector operable to direct the conditioned air over the animal; measuring a temperature of the conditioned air from the air injector using an air temperature sensor; measuring a temperature of the animal's body using an animal temperature sensor; monitoring the temperature of the conditioned air to the animal and the temperature of the animal's body using a controller in communication with an temperature control apparatus, the air temperature sensor, and the animal temperature sensor; and adjusting the temperature of the conditioned air directed over the animal using the temperature control apparatus, the temperature control apparatus comprising: a cooling fan operatively connected to a cooling air line; a heating fan operatively connected to a heating air line; and a heating block operatively connected to the heating fan and the heating air line to heat the air within the heating air line, wherein the cooling air line is connected to the cooling air line inlet and the heating air line is connected to the heating air line inlet.

Embodiment 74: The method of embodiment 73, further comprising measuring the breathing rate of the animal using a pressure sensor.

Embodiment 75: The method of embodiment 73, further comprising adjusting the temperature of the conditioned air flow to correct the temperature of the animal.

Embodiment 76: The method of embodiment 75, wherein the temperature of the conditioned air flow is automatically adjusted using a double PID loop.

Embodiment 77: The method of embodiment 75, wherein adjusting the temperature of the conditioned air flow comprises adjusting a setting of the cooling fan and/or the heating fan.

Embodiment 78: The method of embodiment 75, wherein the heating fan speed is constant to keep the heating block temperature stable.

Embodiment 79: The method of embodiment 75, wherein the speed of the of the cooling fan is adjusted to change the temperature of the conditioned air flow.

Embodiment 80: The method of embodiment 75, wherein the temperature of the air in the cooling air line ranges from 12° C. to 22° C.

Embodiment 81: The method of embodiment 75, wherein the temperature of the air in the heating air line ranges from 35° C. to 50° C.

Embodiment 82: The method of embodiment 75, wherein the temperature of the conditioned air ranges from 32° C. to 40° C.

Embodiment 83: The method of embodiment 82, wherein the conditioned air has a relative humidity ranging from 30% to 50%.

Embodiment 84: The method of embodiment 73, wherein the temperature of the animal needs to be corrected when it falls outside a target temperature range.

Embodiment 85: The method of embodiment 84, wherein the target temperature range is determined for a small animal under anesthesia undergoing imaging to prevent hypothermia due to anesthesia and RF heating due to imaging.

Embodiment 86: The method of embodiment 84, wherein the target temperature range is 32° C. to 40° C.

Embodiment 87: The method of embodiment 84, wherein the conditioned air temperature is warmer than the target temperature range to adjust for the anesthesia and the conditioned air temperature is lower than the target temperature range to adjust for RF heating due to the imaging.

Embodiment 88: The method of embodiment 73, further comprising a display operable to display the temperature of the conditioned air flow.

Embodiment 89: The method of embodiment 88, wherein the display is located on a surface of a tower and the controller is located within the tower.

Embodiment 90: The method of embodiment 88, further comprising connecting the air temperature sensor and the animal temperature sensor to a sensor hub comprising at least two thermocouple ports.

Embodiment 91: The method of embodiment 88, wherein the tower further comprises an animal ID reader in communication with the controller.

Embodiment 92: The method of embodiment 73, further comprising logging data related to the measured temperatures in a server in communication with the controller.

Embodiment 93: The method of embodiment 73, wherein the animal is a non-human animal.

Embodiment 94: The method of embodiment 93, wherein the non-human animal is a mouse or a rat.

Embodiment 95: The method of embodiment 73, wherein the animal is not able to regulate body temperature while under anesthesia for imaging.

Embodiment 96: The method of embodiment 73, wherein the method reduces the incidence of temperature-related mortality.

Embodiment 97: A method of imaging an animal under anesthesia in a controlled temperature environment, the method comprising: placing the animal under anesthesia on an animal bed apparatus; placing the animal bed apparatus with the animal within an imaging system; measuring the temperature of conditioned air from an air injector on the animal bed apparatus using an air temperature sensor; measuring the temperature of the animal's body using an animal temperature sensor; monitoring the temperature of the conditioned air to the animal and the temperature of the animal's body using a controller in communication with a temperature control apparatus, the air temperature sensor, and the animal temperature sensor; and adjusting the temperature of the conditioned air directed over the animal using the temperature control apparatus.

Embodiment 98: The method of embodiment 97, wherein the animal bed apparatus has a base comprising: a cooling air line inlet; a heating air line inlet; an injection zone operable to combine air from the cooling air line and the heating air line, creating conditioned air; and an air injector operable to direct the conditioned air over the animal.

Embodiment 99: The method of embodiment 98, wherein the temperature control apparatus comprises: a cooling fan operatively connected to a cooling air line; a heating fan operatively connected to a heating air line; and a heating block operatively connected to the heating fan and the heating air line to heat the air within the heating air line, wherein the cooling air line is connected to the cooling air line inlet and the heating air line is connected to the heating air line inlet.

Embodiment 100: The method of embodiment 97, further comprising measure the breathing rate of the animal using a pressure sensor.

Embodiment 101: The method of embodiment 97, further comprising adjusting the temperature of the conditioned air flow to correct the temperature of the animal.

Embodiment 102: The method of embodiment 101, wherein the temperature of the conditioned air flow is automatically adjusted using a double PID loop.

Embodiment 103: The method of embodiment 101, wherein adjusting the temperature of the conditioned air flow comprises adjusting a setting of a cooling fan and/or a heating fan of the temperature control apparatus.

Embodiment 104: The method of embodiment 103, wherein the heating fan speed is constant to keep the heating block temperature stable.

Embodiment 105: The method of embodiment 103, wherein the speed of the of the cooling fan is adjusted to change the temperature of the conditioned air flow.

Embodiment 106: The method of embodiment 101, wherein the temperature of the conditioned air ranges from 32° C. to 40° C.

Embodiment 107: The method of embodiment 106, wherein the conditioned air has a relative humidity ranging from 30% to 50%.

Embodiment 108: The method of embodiment 97, wherein the imaging is not compromised within the air flow ranges because of the measuring.

Embodiment 109: The method of embodiment 97, wherein the temperature of the animal needs to be corrected when it falls outside a target temperature range.

Embodiment 110: The method of embodiment 109, wherein the target temperature range is determined for a small animal under anesthesia undergoing imaging to prevent hypothermia due to anesthesia and RF heating due to imaging.

Embodiment 111: The method of embodiment 109, wherein the target temperature range is 32° C. to 40° C.

Embodiment 112: The method of embodiment 109, wherein the conditioned air temperature is warmer than the target temperature range to adjust for the anesthesia and the conditioned air temperature is lower than the target temperature range to adjust for RF heating due to the imaging.

Embodiment 113: The method of embodiment 97, further comprising a display operable to display the temperature of the conditioned air flow.

Embodiment 114: The method of embodiment 113, wherein the display is located on a surface of a tower and the controller is located within the tower.

Embodiment 115: The method of embodiment 114, wherein the tower further comprises an animal ID reader in communication with the controller.

Embodiment 116: The method of embodiment 113, further comprising connecting the air temperature sensor and the animal temperature sensor to a sensor hub comprising at least two thermocouple ports.

Embodiment 117: The method of embodiment 97, further comprising logging data related to the measured temperatures in a server in communication with the controller.

Embodiment 118: The method of embodiment 97, wherein the animal is a non-human animal.

Embodiment 119: The method of embodiment 118, wherein the non-human animal is a mouse or a rat.

Embodiment 120: The method of embodiment 97, wherein the animal is not able to regulate body temperature while under anesthesia for imaging.

Embodiment 121: The method of embodiment 97, wherein the method reduces the incidence of temperature-related mortality.

What is claimed is:

1. A temperature control apparatus for heating or cooling an animal under anesthesia for imaging, the apparatus comprising:

- a cooling fan operatively connected to a cooling air line;
- a heating fan operatively connected to a heating air line;
- a heating block operatively connected to the heating fan and the heating air line to heat the air within the heating air line; and
- a housing, wherein the cooling fan, heating fan, and heating block are located within the housing.

2. The temperature control apparatus of claim 1, wherein the housing further comprises an air inlet operatively connected to the cooling fan to introduce room temperature air into the cooling air line.

3. The temperature control apparatus of claim 1, wherein the housing further comprises a cooling air line outlet and a heating air line outlet.

4. The temperature control apparatus of claim 3, wherein the cooling air line outlet comprises an indicator that air is flowing through the cooling air line and the heating air line outlet comprises an indicator that air is flowing through the heating air line.

5. The temperature control apparatus of claim 4, wherein the indicator on the cooling air line outlet and the indicator on the heating air line outlet is a light surrounding or projecting from the respective outlet.

6. The temperature control apparatus of claim 1, wherein the animal is a non-human animal.

7. The temperature control apparatus of claim 6, wherein the non-human animal is a mouse or a rat.

8. The temperature control apparatus of claim 1, wherein the animal is not able to regulate body temperature while under anesthesia for imaging.

9. The temperature control apparatus of claim 1, further comprising a Peltier cooler connected to the cooling fan.

10. The temperature control apparatus of claim 1, wherein the temperature of the air in the cooling air line ranges from 12° C. to 22° C.

11. The temperature control apparatus of claim 1, wherein the temperature of the air in the heating air line ranges from 35° C. to 50° C.

12. The temperature control apparatus of claim 1, wherein the temperature of a combination of the air in the cooling air line and the heating air line ranges from 32° C. to 40° C.

13. The temperature control apparatus of claim 12, wherein the temperature of the combination of the air in the cooling air line and the heating air line may be changed within 10 seconds after adjusting the cooling fan, the heating fan, and/or the heating block.

14. The temperature control apparatus of claim 13, wherein the change in the temperature of the combination of air changes the temperature of the animal within 1 minute.

15. The temperature control apparatus of claim 12, further comprising a display operable to display the temperature of the air in the cooling air line, the temperature of the air in the heating air line, and/or the temperature of the combination of the air in the cooling air line and the heating air line.

16. The temperature control apparatus of claim 1, wherein the imaging is magnetic resonance imaging (MRI), positron emission tomography (PET), computed tomography (CT), and pulse electron paramagnetic resonance oxygen imaging (EPROI).

17. A system for heating or cooling an animal under anesthesia for imaging, the system comprising:

- a temperature control apparatus comprising:
  - a cooling fan operatively connected to a cooling air line;
  - a heating fan operatively connected to a heating air line;
  - a heating block operatively connected to the heating fan and the heating air line to heat the air within the heating air line; and
  - a housing, wherein the cooling fan, the heating fan, and the heating block are located within the housing;
- an air temperature sensor operable to measure the temperature of a conditioned air flow from the cooling air line and the heating air line;
- an animal temperature sensor operable to measure the temperature of the animal's body; and
- a controller in communication with the temperature control apparatus, the air temperature sensor, and the animal temperature sensor, and operable to monitor the temperature of the conditioned air flow to the animal and the temperature of the animal's body.

18. The system of claim 17, further comprising a pressure sensor operable to measure the breathing rate of the animal.

19. The system of claim 17, wherein the controller is operable to adjust the temperature of the conditioned air flow to correct the temperature of the animal.

20. The system of claim 19, wherein the controller is a proportional-integral-derivative (PID) controller operable to automatically adjust the temperature of the conditioned air flow.

21. The system of claim 19, wherein the controller adjusts a setting of the cooling fan and/or the heating fan to adjust the temperature of the conditioned air flow.

22. The system of claim 19, wherein the heating fan speed is constant to keep the heating block temperature stable.

23. The system of claim 19, wherein the speed of the of the cooling fan is adjusted to change the temperature of the conditioned air flow.

24. The system of claim 19, wherein the temperature of the air in the cooling air line ranges from 12° C. to 22° C.

25. The system of claim 19, wherein the temperature of the air in the heating air line ranges from 35° C. to 50° C.

26. The system of claim 19, wherein the temperature of the conditioned air flow ranges from 32° C. to 40° C.

27. The system of claim 26, wherein the conditioned air has a relative humidity ranging from 30% to 50%.

28. The system of claim 19, wherein the temperature of the animal needs to be corrected when it falls outside a target temperature range.

29. The system of claim 28, wherein the target temperature range is determined for a small animal under anesthesia undergoing imaging to prevent hypothermia due to anesthesia and RF heating due to imaging.

30. The system of claim 28, wherein the target temperature range is 32° C. to 40° C.

31. The system of claim 28, wherein the conditioned air temperature is warmer than the target temperature range to adjust for the anesthesia and the conditioned air temperature is lower than the target temperature range to adjust for RF heating due to the imaging.

32. The system of claim 17, further comprising a display operable to display the temperature of the conditioned air flow.

33. The system of claim 32, further comprising a tower, wherein the display is located on a surface of the tower and the controller is located within the tower.

34. The system of claim 17, wherein the controller is further in communication with a server to log data related to the measured temperatures.

35. The system of claim 17, further comprising a sensor hub with at least two thermocouple ports operable to connect to the air temperature sensor and the animal temperature sensor.

36. The system of claim 17, further comprising an animal ID reader in communication with the controller.

37. The system of claim 17, wherein the animal is a mouse or a rat.

* * * * *